United States Patent [19]
Kochanny et al.

[11] Patent Number: 6,071,912
[45] Date of Patent: Jun. 6, 2000

[54] BENZAMIDINE DERIVATIVES SUBSTITUTED BY AMINO ACID AND HYDROXY ACID DERIVATIVES AND THEIR USE AS ANTI-COAGULANTS

[75] Inventors: Monica Kochanny, San Rafael; Raju Mohan, Moraga; Michael M. Morrissey, Danville; Howard P. Ng, El Sobrante; Weiya Yun, Richmond, all of Calif.

[73] Assignee: Berlex Laboratories, Inc., Richmond, Calif.

[21] Appl. No.: 09/394,458

[22] Filed: Sep. 9, 1999

Related U.S. Application Data

[62] Division of application No. 08/599,834, Feb. 12, 1996, Pat. No. 5,994,375.

[51] Int. Cl.$^7$ .......................... A61K 31/53; C07D 251/26
[52] U.S. Cl. .......................... 514/241; 544/219; 544/216; 544/197; 544/194; 544/180
[58] Field of Search ..................................... 514/241, 245; 544/219, 216, 197, 194, 180

[56] References Cited

U.S. PATENT DOCUMENTS

| | | | |
|---|---|---|---|
| 4,064,169 | 12/1977 | Hamano et al. | 260/564 R |
| 5,332,822 | 7/1994 | Misra | 546/164 |
| 5,451,700 | 9/1995 | Morrissey et al. | 564/165 |
| 5,612,363 | 3/1997 | Mohan et al. | 514/392 |
| 5,633,381 | 5/1997 | Dallas et al. | 546/189 |
| 5,691,364 | 11/1997 | Buckman et al. | 514/341 |
| 5,693,641 | 12/1997 | Buckman et al. | 514/249 |
| 5,726,173 | 3/1998 | Mohan et al. | 514/235.8 |
| 5,726,198 | 3/1998 | Mohan et al. | 514/387 |
| 5,728,697 | 3/1998 | Mohan et al. | 514/235.8 |
| 5,731,308 | 3/1998 | Mohan et al. | 514/219 |
| 5,731,311 | 3/1998 | Mohan et al. | 514/235.8 |
| 5,753,635 | 5/1998 | Buckman et al. | 514/81 |
| 5,846,970 | 12/1998 | Buckman et al. | 514/224.2 |
| 5,846,972 | 12/1998 | Buckman et al. | 514/230.5 |
| 5,849,759 | 12/1998 | Arnaiz et al. | 514/322 |
| 5,859,005 | 1/1999 | Mohan et al. | 514/218 |
| 5,863,914 | 1/1999 | Mohan et al. | 514/231.5 |
| 5,877,181 | 3/1999 | Buckman et al. | 514/269 |
| 5,883,100 | 3/1999 | Buckman et al. | 514/255 |
| 5,889,005 | 3/1999 | Buckman et al. | 514/241 |

FOREIGN PATENT DOCUMENTS

| | | |
|---|---|---|
| 0518818A2 | 6/1992 | European Pat. Off. . |
| 0540051A1 | 10/1992 | European Pat. Off. . |
| 0567966A1 | 4/1993 | European Pat. Off. . |
| 0601459A2 | 12/1993 | European Pat. Off. . |
| 824908 | 12/1959 | United Kingdom . |
| WO93/15756 | 8/1993 | WIPO . |
| WO94/13693 | 6/1994 | WIPO . |
| WO94/17817 | 8/1994 | WIPO . |
| WO96/10022 | 4/1996 | WIPO . |
| WO96/28427 | 9/1996 | WIPO . |
| WO98/11094 | 3/1998 | WIPO . |
| WO98/15547 | 4/1998 | WIPO . |

OTHER PUBLICATIONS

Tidwell, R. et al., "Strategies for Anticoagulation with Synthetic Protease Inhibitors, Xa Inhibitors Versus Thrombin Inhibitors," *Thrombosis Research*, (1980) 19:339–349.

Wagner, G. et al., "Synthese von a–a'–Bis[amidinobenzyliden]–und a–a'Bis–[amidinobenzyl]–cycloalkanonen," *Pharmazie*, (1977) 32, 141–145.

Stürzebecher, J. et al., "Cyclic Amides of Nα–arysulfonylanmioacylated 4–amidinophenylalanine— Tight Binding Inhibitors of Thrombin," *Thrombosis Research*, (1983) 29:635–642.

Kikumoto, R. et al., "Selective inhibition of Thrombin by (2R,4R)–4–Methyl–1–[N$^2$–[(3–methyl–1,2,3, 4–tetrahydro–8–quinolinyl)–sulfonyl]–L–arginyl)]–2piperidinecarboxylic Acid," *Biochemistry*, (1984) 23:85–90.

Stürzebecher, J. et al., "Synthetic Inhibitors of Serine Proteinases XXIII, Inhibition of Factor Xa by Diamidines", *Thrombosis Research*, (1980) 17:545:548.

Chauhan , P. et al., "Effect of new diamidines against *Leishmania donovani* infection," *Indian Journal of Experimental Biology*, (1993) 31:196–198.

Ashley, J. et al., "The Search for Chemotherapeutic Amidines. Part XVI. Amidinoanilino–1,3,5–triazines and Related Compounds", *J. of the Chemical Society*, (1960) 4525:4532.

Geratz, J. et al., "The Inhibition of Urokinase by Aromatic Diamidines" *Thrombos. Diathes haemorrh. (Stuttg.),* (1975)33:230–243.

Geratz, J. et al. "Novel Bis (benzamidino) Compounds with an Aromatic Central Link. Inhibitors of Thrombin, Pancreatic Kallikrein, Trypsin, and Complement" *J. of Medicinal Chemistry*, (1976) 19(5):634–639.

Chauhan, P. et al., "Antiparasitic Agents: Part VI—Synthesis of 1,2–,1,3–&1,4–Bis(4–substituted aryloxy)benzenes & Their Biological Activities", *Indian Journal of Chemistry*, (1988) 27B:38–42.

U.S. Pat. application Ser. No. 09/205,498, filed Dec. 4, 1998, entitled: Aryl Substituted N–Heterocyclic Derivatives as Anti–Coagulants.

U.S. Pat. application Ser. No. 09/187,459, filed Nov. 5, 1998, entitled: Ortho–Anthranilamide Derivatives as Anti- –Coagulants.

U.S. Pat. application Ser. No. 09/196,921, filed Nov. 19, 1998, entitled: Polyhydroxylated Monocyclic N–Heterocyclic Derivatives as Anti–Coagulants.

U.S. Pat. application Ser. No. 08/920,319, filed Aug. 27, 1997, entitled: Benzamidine Derivatives Substituted by Cyclic Amino Acid and Cyclic Hydroxy Acid Derivatives and Their Use as Anti–Coagulants.

*Primary Examiner*—John Kight
*Assistant Examiner*—Charanjit S. Aulakh
*Attorney, Agent, or Firm*—Carol J. Roth

[57] ABSTRACT

This invention is directed to benzamidine derivatives substituted by amino acid and hydroxy acid derivatives which are useful as anti-coagulants. This invention is also directed to pharmaceutical compositions containing the compounds of the invention, and methods of using the compounds to treat disease-states characterized by thrombotic activity.

3 Claims, No Drawings

BENZAMIDINE DERIVATIVES SUBSTITUTED BY AMINO ACID AND HYDROXY ACID DERIVATIVES AND THEIR USE AS ANTI-COAGULANTS

This application is a divisional of U.S. patent application, Ser. No. 08/599,834, filed Feb. 12, 1996, now U.S. Pat. No. 5,994,375.

FIELD OF THE INVENTION

The present invention is directed to monocyclic N-heterocyclics which are substituted by amino acid or hydroxy acid derivatives, and their pharmaceutically acceptable salts, which inhibit the enzyme, factor Xa, thereby being useful as anti-coagulants. It also relates to pharmaceutical compositions containing the derivatives or their pharmaceutically acceptable salts, and methods of their use.

BACKGROUND OF THE INVENTION

Factor Xa is a member of the trypsin-like serine protease class of enzymes. A one-to-one binding of factors Xa and Va with calcium ions and phospholipid forms the prothrombinase complex which converts prothrombin to thrombin. Thrombin, in turn, converts fibrinogen to fibrin which polymerizes to form insoluble fibrin.

In the coagulation cascade, the prothrombinase complex is the convergent point of the intrinsic (surface activated) and extrinsic (vessel injury-tissue factor) pathways (*Biochemistry* (1991), Vol. 30, p. 10363; and *Cell* (1988), Vol. 53, pp. 505–518). The model of the coagulation cascade has been refined further with the discovery of the mode of action of tissue factor pathway inhibitor (TFPI) (*Seminars in Hematology* (1992), Vol. 29, pp. 159–161). TFPI is a circulating multi-domain serine protease inhibitor with three Kunitz-type domains which competes with factor Va for free factor Xa. Once formed, the binary complex of factor Xa and TFPI becomes a potent inhibitor of the factor VIIa and tissue factor complex.

Factor Xa can be activated by two distinct complexes, by tissue factor-VIIa complex on the "Xa burst" pathway and by the factor IXa-VIIIA complex (TENase) of the "sustained Xa" pathway in the coagulation cascade. After vessel injury, the "Xa burst" pathway is activated via tissue factor (TF). Up regulation of the coagulation cascade occurs via increased factor Xa production via the "sustained Xa" pathway. Down regulation of the coagulation cascade occurs with the formation of the factor Xa-TFPI complex, which not only removes factor Xa but also inhibits further factor formation via the "Xa burst" pathway. Therefore, the coagulation cascade is naturally regulated by factor Xa.

The primary advantage of inhibiting factor Xa over thrombin in order to prevent coagulation is the focal role of factor Xa versus the multiple functions of thrombin. Thrombin not only catalyzes the conversion of fibrinogen to fibrin, factor VIII to VIIIA, factor V to Va, and factor XI to XIa, but also activates platelets, is a monocyte chemotactic factor, and mitogen for lymphocytes and smooth muscle cells. Thrombin activates protein C, the in vivo anti-coagulant inactivator of factors Va and VIIIa, when bound to thrombomodulin. In circulation, thrombin is rapidly inactivated by antithrombin III (ATIII) and heparin cofactor II (HCII) in a reaction which is catalyzed by heparin or other proteoglycan-associated glycosaminoglycans, whereas thrombin in tissues is inactivated by the protease, nexin. Thrombin carries out its multiple cellular activation functions through a unique "tethered ligand" thrombin receptor (*Cell* (1991), Vol. 64, p. 1057), which requires the same anionic binding site and active site used in fibrinogen binding and cleavage and by thrombomodulin binding and protein C activation. Thus, a diverse group of in vivo molecular targets compete to bind thrombin and the subsequent proteolytic events will have very different physiological consequences depending upon which cell type and which receptor, modulator, substrate or inhibitor binds thrombin.

Published data with the proteins antistasin and tick anticoagulant peptide (TAP) demonstrate that factor Xa inhibitors are efficacious anti-coagulants (*Thrombosis and Haemostasis* (1992), Vol. 67, pp. 371–376; and *Science* (1990), Vol. 248, pp. 593–596).

The active site of factor Xa can be blocked by either a mechanism-based or a tight binding inhibitor (a tight binding inhibitor differs from a mechanism-based inhibitor by the lack of a covalent link between the enzyme and the inhibitor). Two types of mechanism-based inhibitors are known, reversible and irreversible, which are distinguished by ease of hydrolysis of the enzyme-inhibitor link (*Thrombosis Res* (1992), Vol. 67, pp. 221–231; and *Trends Pharmacol. Sci.* (1987), Vol. 8, pp. 303–307). A series of guanidino compounds are examples of tight-binding inhibitors (*Thrombosis Res.* (1980), Vol. 19, pp. 339–349). Arylsulfonyl-arginine-piperidinecarboxylic acid derivatives have also been shown to be tight-binding inhibitors of thrombin (*Biochem.* (1984), Vol. 23, pp. 85–90), as well as a series of arylamidine-containing compounds, including 3-amidinophenylaryl derivatives (*Thrombosis Res.* (1983), Vol. 29, pp. 635–642) and bis(amidino)benzyl cycloketones (*Thrombosis Res.* (1980), Vol. 17, pp. 545–548). However, these compounds demonstrate poor selectivity for factor Xa.

Related Disclosures

European Published Patent Application 0 540 051 (Nagahara et al.) describes aromatic amidine derivatives which are stated to be capable of showing a strong anticoagulant effect through reversible inhibition of factor Xa.

The synthesis of α,α'-bis(amidinobenzylidene) cycloalkanones and α,α'-bis(amidino-benzyl) cycloalkanones is described in *Pharmazie* (1977), Vol. 32, No. 3, pp. 141–145. These compounds are disclosed as being serine protease inhibitors.

SUMMARY OF THE INVENTION

This invention is directed to compounds or their pharmaceutically acceptable salts which inhibit human factor Xa and are therefore useful as pharmacological agents for the treatment of disease-states characterized by thrombotic activity.

Accordingly, in one aspect, this invention provides compounds selected from the group consisting of the following formulae:

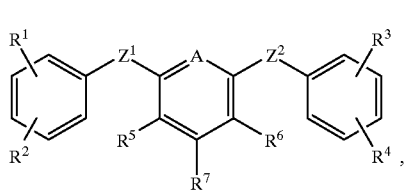

(I)

-continued (II)

(III)

(IV)

(V)

(VI)

and (VII)

wherein:

A is —C(R$^8$)= or —N=;

Z$^1$ and Z$^2$ are independently —O—, —N(R$^{13}$)—, —S—, or —OCH$_2$—;

R$^1$ and R$^4$ are each independently hydrogen, halo, alkyl, nitro, —OR$^{13}$, —C(O)OR$^{13}$, —C(O)N(R$^{13}$)R$^{14}$, —N(R$^{13}$)R$^{14}$, —N(R$^{13}$)C(O)R$^{13}$, or —N(H)S(O)$_2$R$^{16}$;

R$^2$ is —C(NH)NH$_2$, —C(NH)N(H)OR$^{13}$, —C(NH)N(H)C(O)R$^{16}$, —C(NH)N(H)C(O)R$^{13}$, —C(NH)N(H)S(O)$_2$R$^{16}$, or —C(NH)N(H)C(O)N(H)R$^{13}$;

R$^3$ is halo, alkyl, haloalkyl, nitro, amino, ureido, guanidino, —OR$^{13}$, —C(NH)NH$_2$, —C(NH)N(H)OR$^{13}$, —C(O)N(R$^{13}$)R$^{14}$, —R$^{15}$—C(O)N(R$^{13}$)R$^{14}$, —CH(OH)C(O)N(R$^{13}$)R$^{14}$, —N(R$^{13}$)R$^{14}$, —R$^{15}$—N(R$^{13}$)R$^{14}$, —C(O)OR$^{13}$, —R$^{15}$—C(O)OR$^{13}$, —N(R$^{13}$)C(O)R$^{13}$, (1,2)-tetrahydropyrimidinyl (optionally substituted by alkyl), (1,2)-imidazolyl (optionally substituted by alkyl), or (1,2)-imidazolinyl (optionally substituted by alkyl);

R$^5$ and R$^6$ are independently hydrogen, halo, alkyl, haloalkyl, nitro, —N(R$^{13}$)R$^{14}$, —C(O)OR$^{13}$, —C(O)N(R$^{13}$)R$^{14}$, —C(O)N(R$^{13}$)CH$_2$C(O)N(R$^{13}$)R$^{14}$, —N(R$^{13}$)C(O)N(R$^{13}$)R$^{14}$, —N(R$^{13}$)C(O)R$^{14}$, —N(R$^{13}$)S(O)$_2$R$^{16}$ or N(R$^{13}$)C(O)N(R$^{13}$)—CH$_2$C(O)N(R$^{13}$)R$^{14}$;

R$^7$ is —N(R$^9$)—(C(R$^{10}$)(R$^{11}$))$_n$—R$^{12}$ (where n is 1 to 4) or —O—(C(R$^{10}$)(R$^{11}$))$_n$—R$^{12}$ (where n is 1 to 6);

R$^8$ is hydrogen, alkyl or halo;

R$^9$ is hydrogen, alkyl, aryl, aralkyl, —R$^{15}$—C(O)OR$^{13}$, —R$^{15}$—C(O)N(R$^{13}$)R$^{14}$, —R$^{15}$—N(R$^{13}$)R$^{14}$, —R$^{15}$—CH(N(R$^{13}$)R$^{14}$)C(O)OR$^{13}$, or —R$^{15}$—S(O)$_2$R$^{16}$;

each R$^{10}$ is independently alkyl, alkenyl, alkynyl, haloalkyl, haloalkenyl, cycloalkyl, cycloalkylalkyl, —C(O)OR$^{13}$, —R$^{15}$—C(O)OR$^{13}$, —R$^{15}$—C(O)N(R$^{13}$)R$^{14}$, —C(O)—R$^{15}$—N(R$^{13}$)R$^{14}$, —R$^{15}$—C(O)R$^{13}$, —R$^{15}$—C(O)N(R$^{13}$)N(R$^{13}$)R$^{14}$, —R$^{15}$—C(R$^{13}$)(OR$^{13}$)—R$^{15}$—N(R$^{13}$)(R$^{14}$), —C(R$^{13}$)(ORC$^{13}$)C(O)OR$^{14}$, —R$^{15}$—C(R$^{13}$)(C(O)OR$^{13}$)$_2$, —C(R$^{13}$)(N(R$^{13}$)R$^{14}$)C(O)OR$^{13}$, —R$^{15}$—C(R$^{13}$)(N(R$^{13}$)R$^{14}$)C(O)OR$^{13}$, —C(R$^{13}$)(OR$^{13}$)R$^{14}$, —R$^{15}$—N(R$^{13}$)R$^{14}$, —R$^{15}$—N(R$^{13}$)C(O)OR$^{16}$, —R$^{15}$—N(R$^{13}$)C(O)R$^{14}$, —R$^{15}$—N(R$^{13}$)C(NR$^{13}$)R$^{16}$, —R$^{15}$N(R$^{13}$)S(O)$_2$R$^{16}$, —R$^{15}$—N(R$^{13}$)C(O)N(R$^{13}$)R$^{14}$, —R$^{15}$—N(R$^{13}$)C(NR$^{13}$)N(R$^{13}$)R$^{14}$, —R$^{15}$—N(R$^{13}$)C(NR$^{13}$)N(R$^{13}$)N(R$^{13}$)R$^{14}$, —R$^{15}$—N(R$^{13}$)—R$^{15}$—C(R$^{13}$)(N(R$^{13}$)R$^{14}$)C(O)OR$^{13}$, —R$^{15}$—N(R$^{13}$)S(O)R$^{14}$, —R$^{15}$OR$^{13}$, —R$^{15}$—ON(R$^{13}$)C(NR$^{13}$)N(R$^{13}$)R$^{14}$, —R$^{15}$—OS(O)$_2$OR$^{13}$, —R$^{15}$P(O)(OR$^{13}$)R$^{14}$, —R$^{15}$—OP(O)(OR$^{13}$)$_2$, —R$^{15}$—P(O)(OR$^{13}$)$_2$, —R$^{15}$—SR$^{13}$, —R$^{15}$—S—R$^{15}$—C(O)OR$^{13}$, —R$^{15}$—S—R$^{15}$—N(R$^{13}$)R$^{14}$, —R$^{15}$—S—R$^{15}$—C(R$^{13}$)(N(R$^{13}$)R$^{14}$)C(O)OR$^{13}$, —R$^{15}$—S—R$^{15}$—N(R$^{13}$)C(O)OR$^{13}$, —R$^{15}$—S—R$^{15}$—N(R$^{13}$)C(O)R$^{13}$, —R$^{15}$—S—S—R$^{15}$—C(R$^{13}$)(N(R$^{13}$)R$^{14}$)C(O)OR$^{13}$, —R$^{15}$—SC(O)N(R$^{13}$)R$^{14}$, —R$^{15}$SC(S)N(R$^{13}$)R$^{14}$, —R$^{15}$—S(O)R$^{13}$, —R$^{15}$—S(O)$_2$R$^{16}$, —R$^{15}$—S(O)OR$^{13}$, —R$^{15}$—S(O)$_2$OR$^{13}$, —R$^{15}$—S(O)$_2$N(R$^{13}$)R$^{14}$, —R$^{15}$—S(O)(NR$^{13}$)R$^{14}$, or each R$^{10}$ is aryl (optionally substituted by one or more substituents selected from the group consisting of alkyl, halo, haloalkyl, haloalkoxy, nitro, —OR$^{13}$, —SR$^{13}$, —N(R$^{13}$)R$^{14}$, —C(O)OR$^{13}$, —C(O)N(R$^{13}$)R$^{14}$, —S(O)$_2$OR$^{13}$ and —OP(O)(OR$^{13}$)$_2$), or each R$^{10}$ is aralkyl (optionally substituted by one or more substituents selected from the group consisting of alkyl, halo, haloalkyl, haloalkoxy, cyano, nitro, —OR$^{13}$, —SR$^{13}$, —N(R$^{13}$)R$^{14}$, —C(O)OR$^{13}$, —C(O)N(R$^{13}$)R$^{14}$, —S(O)OR$^{13}$, and —OP(O)(OR$^{13}$)$_2$), or each R$^{10}$ is heterocyclyl (optionally substituted by one or more substituents selected from the group consisting of alkyl, halo, haloalkyl, haloalkoxy, aralkyl, —OR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$), or each R$^{10}$ is heterocyclylalkyl (where the heterocyclyl radical is optionally substituted by one or more substituents selected from the group consisting of alkyl, halo, haloalkyl, haloalkoxy, aralkyl, —OR$^{13}$, —SR$^{13}$, —C(O)OR$^{13}$, —N(R$^{13}$)R$^{14}$, —C(O)N(R$^{13}$)R$^{14}$), —S(O)$_2$OR$^{13}$ and —OP(O)(OR$^{13}$)$_2$), or each R$^{10}$ is adamantyl (optionally substituted by alkyl, halo, haloalkyl, haloalkoxy, —OR$^{13}$, —SR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$), or each R$^{10}$ is adamantylalkyl (where the adamantyl radical is optionally substituted by alkyl, halo, haloalkyl, haloalkoxy, —OR$^{13}$, —SR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$);

each R$^{11}$ is independently hydrogen, alkyl, cycloalkyl, or aryl;

R$^{12}$ is —C(O)OR$^{13}$ or —C(O)N(R$^{13}$)R$^{14}$;

each R$^{13}$ and R$^{14}$ is independently hydrogen, alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);

R$^{15}$ is a straight or branched alkylene chain; and

R$^{16}$ is alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);

as a single stereoisomer or a mixture thereof; or a pharmaceutically acceptable salt thereof.

In another aspect, this invention provides compositions useful in treating a human having a disease-state characterized by thrombotic activity, which composition comprises a therapeutically effective amount of a compound of the invention as described above, or a pharmaceutically acceptable salt thereof, and a pharmaceutically acceptable excipient.

In another aspect, this invention provides a method of treating a human having a disease-state characterized by thrombotic activity, which method comprises administering to a human in need thereof a therapeutically effective amount of a compound of the invention as described above.

In another aspect, this invention provides a method of treating a human having a disease-state alleviated by the inhibition of factor Xa, which method comprises administering to a human in need thereof a therapeutically effective amount of a compound of the invention as described above.

In another aspect, this invention provides a method of inhibiting human factor Xa in vitro or in vivo by the administration of a compound of the invention.

DETAILED DESCRIPTION OF THE INVENTION

Definitions

As used in the specification and appended claims, unless specified to the contrary, the following terms have the meaning indicated:

"Alkyl" refers to a straight or branched chain monovalent or divalent radical consisting solely of carbon and hydrogen, containing no unsaturation and having from one to six carbon atoms, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched chain monovalent or divalent radical consisting solely of carbon and hydrogen, containing at least one double bond and having from one to six carbon atoms, e.g., ethenyl, prop-1-enyl, but-1-enyl, pent-1-enyl, penta-1,4-dienyl, and the like.

"Alkynyl" refers to a straight or branched chain monovalent or divalent radical consisting solely of carbon and hydrogen, containing at least one triple bond and having from one to six carbon atoms, e.g., ethynyl, prop-1-ynyl, but-1-ynyl, pent-1-ynyl, pent-3-ynyl, and the like.

"Alkoxy" refers to a radical of the formula —OR$_a$ where R$_a$ is alkyl as defined above, e.g., methoxy, ethoxy, n-propoxy, 1-methylethoxy (iso-propoxy), n-butoxy, n-pentoxy, 1,1-dimethylethoxy (t-butoxy), and the like.

"Alkylene" refers to straight or branched chain divalent radical consisting solely of carbonyl and hydrogen, containing no unsaturation and having from one to six carbon atoms, e.g., methylene, ethylene, propylene, n-butylene, and the like.

"Aryl" refers to a phenyl or naphthyl radical.

"Aralkyl" refers to a radical of the formula —R$_a$R$_b$ where R$_a$ is alkyl as defined above and R$_b$ is aryl as defined above, e.g., benzyl.

"Aryloxy" refers to a radical of the formula —OR$_b$ where R$_b$ is aryl as defined above, e.g., phenoxy and naphthoxy.

"Aralkoxy" refers to a radical of the formula —OR$_c$ where R$_c$ is aralkyl as defined above, e.g., benzyloxy, and the like.

"Alkoxyalkyl" refers to a radical of the formula —R$_a$OR$_a$ where each R$_a$ is independently an alkyl radical as defined above, e.g., methoxyethyl, ethoxymethyl, propoxymethyl, propoxyethyl, and the like.

"Alkoxyalkenyl" refers to a radical of the formula —R$_d$OR$_a$ where R$_a$ is alkyl as defined above and R$_d$ is alkenyl as defined above, e.g., methoxyethenyl, methoxyprop-1-enyl, ethoxybut-1-enyl, propoxypent-1-enyl, ethoxypent-1,4-dienyl, and the like.

"Alkoxyalkynyl" refers to a radical of the formula —R$_e$OR$_a$ where R$_a$ is alkyl as defined above and R$_e$ is alkynyl as defined above, e.g., ethoxyethynyl, methoxyprop-1-ynyl, propoxybut-1-ynyl, ethoxypent-1-ynyl, methoxypent-3-ynyl, and the like.

"Alkoxycarbonylalkenyl" refers to a radical of the formula —R$_d$C(O)OR$_a$ where R$_a$ is an alkyl radical as defined above and R$_d$ is an alkenyl radical as defined above, e.g., ethoxycarboxyethenyl, 3-methoxycarbonylprop-1-enyl, 4-t-butoxycarbonylbut-1-enyl, 5-ethoxycarbonylpent-1-enyl, 5-t-butoxycarbonylpenta-1,4-dienyl, and the like.

"Alkoxycarbonylalkynyl" refers to a radical of the formula —R$_e$C(O)OR$_a$ where R$_a$ is an alkyl radical as defined above and R$_e$ is an alkynyl radical as defined above, e.g., 3-methoxycarbonylprop-1-ynyl, 4-t-butoxycarbonylbut-1-ynyl, 5-ethoxycarbonylpent-1-ynyl, 5-t-butoxycarbonylpent-3-ynyl, and the like.

"Aryloxycarbonylalkenyl" refers to a radical of the formula —R$_d$C(O)OR$_b$ where R$_b$ is an aryl radical as defined above and R$_d$ is an alkenyl radical as defined above, e.g., phenoxycarboxyethenyl, phenoxycarbonylprop-1-enyl, 4-phenoxycarbonylbut-1-enyl, 5-naphthoxycarbonylpent-1-enyl, 5-phenoxycarbonylpenta-1,4-dienyl, and the like.

"Aryloxycarbonylalkynyl" refers to a radical of the formula —R$_e$C(O)OR$_b$ where R$_b$ is an aryl radical as defined above and R$_e$ is an alkynyl radical as defined above, e.g., 3-phenoxycarbonylprop-1-ynyl, 4-phenoxycarbonylbut-1-ynyl, 5-phenoxycarbonylpent-1-ynyl, 5-phenoxycarbonylpent-3-ynyl, and the like.

"Amidino" refers to the radical —C(NH)—NH$_2$.

"Carboxyalkenyl" refers to an alkenyl radical as defined above, that is substituted by a carboxy radical, e.g., 3-carboxyprop-1-enyl, 4-carboxybut-1-enyl, 4-carboxypent-1-enyl, 5-carboxypenta-1,4-dienyl, and the like.

"Carboxyalkynyl" refers to an alkynyl radical as defined above, that is substituted by a carboxy radical, e.g., 3-carboxyprop-1-ynyl, 4-carboxybut-1-ynyl, 5-carboxypent-1-ynyl, 5-carboxypent-3-ynyl, and the like.

"Cycloalkyl" refers to a stable 3- to 7-membered monocyclic cyclic radical which is saturated, and which consist solely of carbon and hydrogen atoms, e.g., cyclopropyl, cyclobutyl, cyclobutyl, cyclohexyl, and the like.

"Dialkylamino" refers to a radical of the formula —NR$_a$R$_a$ where each R$_a$ is independently an alkyl radical as defined above, e.g., dimethylamino, methylethylamino, diethylamino, dipropylamino, ethylpropylamino, and the like.

"Dialkylaminocarbonyl" refers to a radical of the formula —C(O)NR$_a$R$_a$ where each R$_a$ is independently an alkyl radical as defined above, e.g., dimethylaminocarbonyl, methylethylaminocarbonyl, diethylaminocarbonyl, dipropylaminocarbonyl, ethylpropylaminocarbonyl, and the like.

"Halo" refers to bromo, chloro or fluoro.

"Haloalkyl" refers to an alkyl radical, as defined above, that is substituted by one or more halo radicals, as defined above, e.g., trifluoromethyl, difluoromethyl, trichloromethyl, 2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —OR$_f$ where R$_f$ is haloalkyl as defined above, e.g., trifluoromethoxy, difluoromethoxy, trichloromethoxy, 2-trifluoroethoxy, 1-fluoromethyl-2-fluoroethoxy, 3-bromo-2-fluoropropoxy, 1-bromomethyl-2-bromoethoxy, and the like.

"Haloalkenyl" refers to an alkenyl radical as defined above, that is substituted by one or more halo radicals, e.g., bromoethenyl, 3-trifluoroprop-1-enyl, bromobut-1-enyl, chloropent-1-enyl, bromopenta-1,4-dienyl, and the like.

"Haloalkynyl" refers to an alkynyl radical as defined above, that is substituted by one or more halo radicals, e.g., bromoethynyl, 3-trifluoroprop-1-ynyl, bromobut-1-ynyl, chloropent-1-ynyl, bromopenta-1,4-diynyl, and the like.

"Haloalkoxyalkyl" refers to a radical of the formula —R$_a$OR$_a$ where each R$_a$ is independently an alkyl radical as defined above, that is substituted by one or more halo radicals on the alkoxy radical, e.g., bromomethoxyethyl, chloroethoxymethyl, 3-trifluoropropoxymethyl, bromopropoxyethyl, and the like.

"Haloalkoxyalkenyl" refers to a radical of the formula —R$_d$OR$_a$ where R$_a$ is alkyl as defined above and R$_d$ is alkenyl as defined above, that is substituted by one or more halo radicals, e.g., bromomethoxyethenyl, chloromethoxyprop-1-enyl, chloroethoxybut-1-enyl, 3-trifluoropropoxypent-1-enyl, chloroethoxypenta-1,4-dienyl, and the like.

"Haloalkoxyalkynyl" refers to a radical of the formula —R$_e$OR$_a$ where R$_a$ is alkyl as defined above and R$_e$ is alkynyl as defined above, that is substituted by one or more halo radicals, e.g., bromoethoxyethynyl, chloromethoxyprop-1-ynyl, 3-trifluoropropoxybut-1-ynyl, bromoethoxypent-1-ynyl, chloromethoxypent-3-ynyl, and the like.

"Hydroxyalkenyl" refers to an alkenyl radical as defined above, that is substituted by a hydroxy radical, e.g., 3-hydroxyprop-1-enyl, 4-hydroxybut-1-enyl, 4-hydroxypent-1-enyl, 5-hydroxypenta-1,4-dienyl, and the like.

"Hydroxyalkynyl" refers to an alkynyl radical as defined above, that is substituted by a hydroxy radical, e.g., 3-hydroxyprop-1-ynyl, 4-hydroxybut-1-ynyl, 5-hydroxypent-1-ynyl, 5-hydroxypent-3-ynyl, and the like.

"Haloalkoxycarbonylalkyl" refers to a radical of the formula —R$_a$C(O)OR$_a$ where each R$_a$ is independently an alkyl radical as defined, where the terminal alkyl radical is substituted by one or more halo radicals, e.g., bromoethoxycarbonylethyl, 3-chloropropoxycarbonylethyl, 4-bromobutoxycarbonylethyl, and the like.

"Haloalkoxycarbonylalkenyl" refers to a radical of the formula —R$_d$C(O)OR$_a$ where R$_a$ is an alkyl radical as defined that is substituted by one or more halo radicals, and R$_d$ is alkenyl as defined above, e.g., bromomethoxycarbonylethenyl, 3-chloroethoxycarbonylprop-1-enyl, 4-(2-bromoethoxycarbonyl)but-1-enyl, 5-(3-chloropropoxycarbonyl)pent-1-enyl, and the like.

"Haloalkoxycarbonylalkynyl" refers to a radical of the formula —R$_e$C(O)OR$_a$ where R$_a$ is an alkyl radical as defined that is substituted by one or more halo radicals, and R$_e$ is alkynyl as defined above, e.g., 3-(2-chloroethoxycarbonyl)prop-1-ynyl, 4-(3-chloropropoxycarbonyl)but-1-ynyl, 5-(2-bromoethoxycarbonyl)pent-1-ynyl, and the like.

"Heterocyclyl" refers to a stable 3- to 10-membered monocyclic or bicyclic radical which is either saturated or unsaturated, and which consists of carbon atoms and from one to three heteroatoms selected from the group consisting of nitrogen, oxygen and sulfur, and wherein the nitrogen, carbon or sulfur atoms may be optionally oxidized, and the nitrogen atom may be optionally quaternized. The heterocyclyl radical may be attached to the main structure at any heteroatom or carbon atom which results in the creation of a stable structure. Examples of such heterocyclic radicals include, but are not limited to, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridinyl, pyrazinyl, pyrimidinyl, pyridazinyl, oxazolyl, oxazolidinyl, triazolyl, indanyl, isoxazolyl, isoxazolidinyl, morpholinyl, thiazolyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Preferred heterocyclyl radicals in this invention are indolyl, imidazolyl, thiazolyl, isoxazolyl, triazolyl, pyridinyl, thienyl, benzothienyl, furyl, and 3,4-dihydro-2,3-dioxo-1(2H)-pyrimidinyl.

"Heterocyclylalkyl" refers to a radical of the formula —R$_a$R$_g$ where R$_a$ is an alkyl radical as defined above and R$_g$ is a heterocyclyl radical as defined above, e.g., indolinylmethyl or imidazolylmethyl, and the like.

"(1,2)-Imidazolyl" refers to an imidazolyl radical attached at either the 1- or 2-position.

"(1,2)-Imidazolinyl" refers to a 4,5-dihydroimidazolyl radical attached at either the 1- or the 2-position.

"Monoalkylamino" refers to a radical of the formula —NHR$_a$ where R$_a$ is an alkyl radical as defined above, e.g., methylamino, ethylamino, propylamino, and the like.

"Monoalkylaminocarbonyl" refers to a radical of the formula —C(O)NHR$_a$ where R$_a$ is an alkyl radical as defined above, e.g., methylaminocarbonyl, ethylaminocarbonyl, propylaminocarbonyl, and the like.

"(1,2)-Tetrahydropyrimidinyl" refers to a tetrahydropyrimidinyl attached at either the 1- or 2-position.

"Adamantylalkyl" refers to a radical of the formula —R$_a$R$_h$ where R$_a$ is an alkyl radical as defined above, and R$_h$ is an adamantyl radical, e.g., adamantylmethyl, 2-adamantylethyl, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethamine, dicyclohexylamine, choline and caffeine.

"Therapeutically effective amount" refers to that amount of a compound of formula (I) which, when administered to a human in need thereof, is sufficient to effect treatment, as defined below, for disease-states characterized by thrombotic activity. The amount of a compound of formula (I) which constitutes a "therapeutically effective amount" will vary depending on the compound, the disease-state and its severity, and the age of the human to be treated, but can be determined routinely by one of ordinary skill in the art having regard to his own knowledge and to this disclosure.

"Treating" or "treatment" as used herein cover the treatment of a disease-state in a human, which disease-state is characterized by thrombotic activity; and include:

(i) preventing the disease-state from occurring in a human, in particular, when such human is predisposed to the disease-state but has not yet been diagnosed as having it;

(ii) inhibiting the disease-state, i.e., arresting its development; or (iii) relieving the disease-state, i.e., causing regression of the disease-state.

The yield of each of the reactions described herein is expressed as a percentage of the theoretical yield. The compounds of the invention, or their pharmaceutically acceptable salts, may have asymmetric carbon atoms in their structure. The compounds of the invention and their pharmaceutically acceptable salts may therefore exist as single stereoisomers, racemates, and as mixtures of enantiomers and diastereomers. All such single stereoisomers, racemates and mixtures thereof are intended to be within the scope of this invention.

The nomenclature used herein is a modified form of the I.U.P.A.C. system wherein the compounds of the invention are named as derivatives of benzamidine. For example, a compound of the invention selected from formula (I), i.e.,

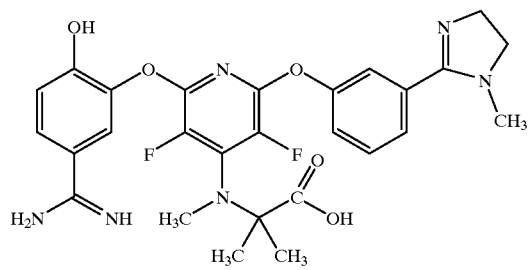

wherein A is —N═; $Z^1$ and $Z^2$ are both —O—; $R^1$ is hydroxy; $R^2$ is —C(NH)NH$_2$; $R^3$ is 1-methylimidazolin-2-yl; $R^4$ is hydrogen; $R^5$ and $R^6$ are both fluoro; $R^7$ is —N($R^9$)—(C($R^{10}$)($R^{11}$))$_n$—$R^{12}$ where n is 1, $R^9$ is methyl, $R^{10}$ is methyl, $R^{11}$ is methyl and $R^{12}$ is —C(O)O$R^{13}$ where $R^{13}$ is hydrogen, namely, 4-hydroxy-3-[(4-(N-(1-carboxy-1-methylethyl)amino)-6-(3-(1-methyl)imidazolin-2-yl)phenoxy-3,5-difluoropyridin-2-yl)-oxy]benzamidine.

Utility and Administration

A. Utility

The compounds of the invention are inhibitors of factor Xa and therefore useful in disease-states characterized by thrombotic activity based on factor Xa's role in the coagulation cascade (see Background of the Invention above). A primary indication for the compounds is prophylaxis for long term risk following myocardial infarction. Additional indications are prophylaxis of deep vein thrombosis (DVT) following orthopedic surgery or prophylaxis of selected patients following a transient ischemic attack. The compounds of the invention may also be useful for indications in which coumarin is currently used, such as for DVT or other types of surgical intervention such as coronary artery bypass graft and percutaneous transluminal coronary angioplasty. The compounds are also useful for the treatment of thrombotic complications associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis. The compounds are also useful for prophylaxis for thrombotic diseases, in particular in patients who have a high risk of developing such disease.

In addition, the compounds of the invention are useful as in vitro and in vivo diagnostic reagents for selectively inhibiting factor Xa without inhibiting other components of the coagulation cascade.

B. Testing

The primary bioassays used to demonstrate the inhibitory effect of the compounds of the invention on factor Xa are simple chromogenic assays involving only serine protease, the compound of the invention to be tested, substrate and buffer (see, e.g., *Thrombosis Res.* (1979), Vol. 16, pp. 245–254). For example, four tissue human serine proteases can be used in the primary bioassay, free factor Xa, prothrombinase, thrombin (IIa) and tissue plasminogen activator (tPA). The assay for tPA has been successfully used before to demonstrate undesired side effects in the inhibition of the fibrinolytic process (see, e.g., *J. Med. Chem.* (1993), Vol. 36, pp. 314–319).

Another bioassay useful in demonstrating the utility of the compounds of the invention in inhibiting factor Xa demonstrates the potency of the compounds against free factor Xa in citrated plasma. For example, the anticoagulant efficacy of the compounds of the invention will be tested using either the prothrombin time (PT), or activated partial thromboplastin time (aPTT) while selectivity of the compounds is checked with the thrombin clotting time (TCT) assay. Correlation of the $K_i$ in the primary enzyme assay with the $K_i$ for free factor Xa in citrated plasma will screen against compounds which interact with or are inactivated by other plasma components. Correlation of the $K_i$ with the extension of the PT is a necessary in vitro demonstration that potency in the free factor Xa inhibition assay translates into potency in a clinical coagulation assay. In addition, extension of the PT in citrated plasma can be used to measure duration of action in subsequent pharmacodynamic studies.

For further information on assays to demonstrate the activity of the compounds of the invention, see R. Lottenberg et al., *Methods in Enzymology* (1981), Vol. 80, pp. 341–361, and H. Ohno et al., *Thrombosis Research* (1980), Vol. 19, pp. 579–588.

C. General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences,* 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state alleviated by the inhibition of factor Xa in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

Preferred Embodiments

Of the compounds of the invention as set forth above in the Summary of the Invention, several groups of compounds are preferred.

One preferred group of compounds contains those compounds selected from formula (I):

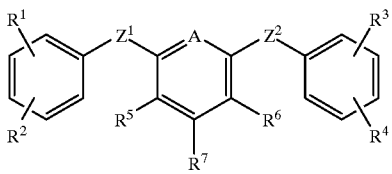

(I)

as single stereoisomers or as mixtures thereof; or a pharmaceutically acceptable salt thereof.

Of this group of compounds, a preferred subgroup of compounds is that subgroup wherein A is —N=; $Z^1$ and $Z^2$ are independently —O—, —S— or —OCH$_2$—; $R^1$ and $R^4$ are independently hydrogen, halo or —OR$^{13}$; $R^2$ is —C(NH)NH$_2$, —C(NH)N(H)S(O)$_2$R$^{16}$, or —C(NH)N(H)C(O)N(H)R$^{13}$; $R^3$ is ureido, guanidino, —N(R$^{13}$)R$^{14}$, —N(H)C(O)R$^{13}$, (1,2)-tetrahydropyrimidinyl (optionally substituted by alkyl), (1,2)-imidazolyl (optionally substituted by alkyl) or (1,2)—imidazolinyl (optionally substituted by alkyl); $R^5$ and $R^6$ are independently hydrogen, halo, alkyl or haloalkyl; $R^7$ is —N(R$^9$)—(C(R$^{10}$)(R$^{11}$))$_n$—R$^{12}$ (where n is 4); $R^9$ is hydrogen, alkyl, aryl, or aralkyl; each $R^{10}$ is independently alkyl, —R$^{15}$—N(R$^{13}$)C(O)N(R$^{13}$)R$^{14}$, —R$^{15}$—N(R$^{13}$)C(NR$^{13}$)N(R$^{13}$)R$^{14}$, —R$^{15}$—N(R$^{13}$)C(NR$^{13}$)R$^{16}$, —R$^{15}$—C(O)OR$^{13}$, —R$^{15}$—C(O)N(R$^{13}$)R$^{14}$, —R$^{15}$—C(R$^{13}$)(C(O)OR$^{13}$)$_2$, —R$^{15}$—N(R$^{13}$)R$^{14}$, —R$^{15}$—SR$^{13}$, —R$^{15}$OR$^{13}$, —R$^{15}$—S(O)$_2$R$^{16}$, —R$^{15}$—OP(O)(OR$^{13}$)$_2$, or each $R^{10}$ is aralkyl (optionally substituted by one or more substituents selected from the group consisting of alkyl, halo, haloalkyl, haloalkoxy, cyano, —OR$^{13}$, —N(R$^{13}$)R$^{14}$, —C(O)OR$^{13}$, —C(O)N(R$^{13}$)R$^{14}$, —SR$^{13}$, —S(O)$_2$OR$^{13}$, and —OP(O)(OR$^{13}$)$_2$), or each $R^{10}$ is heterocyclylalkyl (where the heterocyclyl radical is optionally substituted by one or more substituents selected from the group consisting of alkyl, halo, haloalkyl, haloalkoxy, cyano, —OR$^{13}$, —C(O)OR$^{13}$, —N(R$^{13}$)R$^{14}$, —C(O)N(R$^{13}$)R$^{14}$, —SR$^{13}$, —S(O)$_2$OR$^{13}$, and —OP(O)(OR$^{13}$)$_2$); each $R^{11}$ is independently hydrogen or alkyl; $R^{12}$ is —C(O)OR$^{13}$ or —C(O)N(R$^{13}$)R$^{14}$; each $R^{13}$ and $R^{14}$ is independently hydrogen, alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl); $R^{15}$ is a straight or branched alkylene chain; and $R^{16}$ is alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl).

Of this subgroup of compounds, a preferred class of compounds is that class wherein $Z^1$ and $Z^2$ are each —O—; $R^1$ is hydrogen or —OR$^{13}$; $R^2$ is —C(NH)NH$_2$; $R^3$ is (1,2)-tetrahydropyrimidinyl (optionally substituted by methyl), (1,2)-imidazolyl (optionally substituted by methyl) or (1,2)-imidazolinyl (optionally substituted by methyl); $R^4$ is hydrogen; $R^5$ and $R^6$ are each halo; $R^7$ is —N(R$^9$)—(C(R$^{10}$)(R$^{11}$))$_n$—R$^{12}$ (where n is 1); $R^9$ is hydrogen, alkyl, aryl, or aralkyl; $R^{10}$ is alkyl, —R$^{15}$—N(R$^{13}$)C(O)N(R$^{13}$)R$^{14}$, —R$^{15}$—N(R$^{13}$)C(NR$^{13}$)N(R$^{13}$)R$^{14}$, —R$^{15}$—N(R$^{13}$)C(NR$^{13}$)R$^{16}$, —R$^{15}$—C(O)OR$^{13}$, —R$^{15}$—C(O)N(R$^{13}$)R$^{14}$, —R$^{15}$—C(R$^{13}$)(C(O)OR$^{13}$)$_2$, —R$^{15}$—N(R$^{13}$)R$^{14}$, —R$^{15}$—SR$^{13}$, —R$^{15}$OR$^{13}$, —R$^{15}$—S(O)$_2$R$^{16}$, —R$^{15}$—OP(O)(OR$^{13}$)$_2$, or $R^{10}$ is aralkyl (optionally substituted by one or more substituents selected from the group consisting of halo, haloalkyl, hydroxy, or —OP(O)(OR$^{13}$)$_2$), or $R^{10}$ is imidazolylalkyl, or indolylalkyl; $R^{11}$ is hydrogen or alkyl; $R^{12}$ is —C(O)OR$^{13}$ or —C(O)N(R$^{13}$)R$^{14}$; each $R^{13}$ and $R^{14}$ is independently hydrogen or alkyl; $R^{15}$ is a straight or branched alkylene chain; and $R^{16}$ is alkyl or aryl.

Of this class of compounds, a preferred subclass of compounds is that subclass of compounds wherein $R^1$ is —OR$^{13}$; $R^3$ is (1,2)-imidazolyl (optionally substituted by methyl) or (1,2)-imidazolinyl (optionally substituted by methyl); $R^5$ and $R^6$ are both fluoro; $R^9$ is hydrogen or alkyl; $R^{10}$ is alkyl, —R$^{15}$—N(R$^{13}$)C(O)N(R$^{13}$)R$^{14}$, —R$^{15}$—N(R$^{13}$)C(NR$^{13}$)R$^{16}$ or —R$^{15}$N(R$^{13}$)C(NR$^{13}$)N(R$^{13}$)R$^{14}$; $R^{11}$ is hydrogen or alkyl; and $R^{12}$ is —C(O)OR$^{13}$.

Preferred compounds of this subclass of compounds are selected from the following:

4-hydroxy-3-[(4-(N-methyl-N-(1-ethoxycarbonyl-1-methylethyl)amino)-6-(3-(1-methyl)imidazolin-2-yl)phenoxy-3,5-difluoropyridin-2-yl)oxy]benzamidine;

4-hydroxy-3-[(4-(N-(1-carboxy-5-guanidinopentyl)amino)-6-(3-(1-methyl)imidazolin-2-yl)phenoxy-3,5-difluoropyridin-2-yl)oxy]benzamidine;

4-hydroxy-3-[(4-(N-methyl-N-(1-ethoxycarbonylethyl)amino)-6-(3-(1-methyl)imidazolin-2-yl)phenoxy-3,5-difluoropyridin-2-yl)oxy]benzamidine;

4-hydroxy-3-[(4-(N-methyl-N-(1-carboxy-1-methylethyl)amino)-6-(3-(1-methyl)imidazolin-2-yl)phenoxy-3,5-difluoropyridin-2-yl)oxy]benzamidine;

4-hydroxy-3-[(4-(N-methyl-N-(1-carboxyethyl)amino)-6-(3-(1-methyl)imidazolin-2-yl)phenoxy-3,5-difluoropyridin-2-yl)oxy]benzamidine;

4-hydroxy-3-[(4-(N-(1-carboxy-5-aminopentyl)amino)-6-(3-(1-methyl)imidazolin-2-yl)phenoxy-3,5-difluoropyridin-2-yl)oxy]benzamidine;

4-hydroxy-3-[(4-(N-(1-carboxy-5-guanidinopentyl)amino)-6-(3-(1-methyl)imidazol-2-yl)phenoxy-3,5-difluoropyridin-2-yl)oxy]benzamidine;

4-hydroxy-3-[(4-(N-(1-carboxy-5-(N-(1-iminoethyl)amino)pentyl)amino)-6-( 3-(1-methyl)imidazolin-2-yl)phenoxy-3,5-difluoropyridin-2-yl)oxy]benzamidine; and 4-hydroxy-3-[(4-(N-(1-carboxy-5-(N-(1-iminoethyl)amino)pentyl)amino)-6-(3-(1-methyl) imidazol-2-yl)phenoxy-3,5-difluoropyridin-2-yl)oxy]benzamidine.

Another preferred subgroup of this group of compounds is that subgroup wherein A is —N=; $Z^1$ and $Z^2$ are independently —O—, —S— or —OCH$_2$—; $R^1$ and $R^4$ are independently hydrogen, halo or —OR$^{13}$; $R^2$ is —C(NH)NH$_2$, —C(NH)N(H)S(O)$_2$R$^{16}$, or —C(NH)N(H)C(O)N(H)R$^{13}$; $R^3$ is ureido, guanidino, —N(R$^{13}$)R$^{14}$, —N(H)C(O)R$^{13}$, (1,2)-tetrahydropyrimidinyl (optionally substituted by alkyl), (1,2)-imidazolyl (optionally substituted by alkyl) or (1,2)—imidazolinyl (optionally substituted by alkyl); $R^5$ and $R^6$ are independently hydrogen, halo, alkyl or haloalkyl; $R^7$ is —O—(C(R$^{10}$)(R$^{11}$))$_n$—R$^{12}$ (where n is 1 to 6); each $R^{10}$ is independently alkyl —R$^{15}$—N(R$^{13}$)C(O)N(R$^{13}$)R$^{14}$, —R$^{15}$—N(R$^{13}$)C(NR$^{13}$)N(R$^{13}$)R$^{14}$, —R$^{15}$—N(R$^{13}$)C(NR$^{13}$)R$^{16}$, —R$^{15}$—C(O)OR$^{13}$, —R$^{15}$—C(O)N(R$^{13}$)R$^{14}$, —R$^{15}$—C(R$^{13}$)(C(O)OR$^{13}$)$_2$, —R$^{15}$—N(R$^{13}$)R$^{14}$, —R$^{15}$—SR$^{13}$, —R$^{15}$OR$^{13}$, —R$^{15}$—S(O)$_2$R$^{16}$, —R$^{15}$—OP(O)(OR$^{13}$)$_2$, or each $R^{10}$ is aralkyl (optionally substituted by one or more substituents selected from the group consisting of alkyl, halo, haloalkyl, haloalkoxy, cyano, —$OR^3$, —$N(R^{13})R^{14}$, —$C(O)OR^{13}$, —$C(O)N(R^{13})R^{14}$, —$SR^{13}$, —$S(O)_2OR^{13}$, and —$OP(O)(OR^{13})_2$), or each $R^{10}$ is heterocyclylalkyl (where the heterocyclyl radical is optionally substituted by one or more substituents selected from the group consisting of alkyl, halo, haloalkyl, haloalkoxy, cyano, —$OR^{13}$, —$C(O)OR^{13}$, —$N(R^{13})R^{14}$, —$C(O)N(R^{13})R^{14}$, —$SR^{13}$, —$S(O)_2OR^{13}$, and —$OP(O)(OR^{13})_2$); each $R^{11}$ is independently hydrogen or alkyl; $R^{12}$ is —$C(O)OR^{13}$ or —$C(O)N(R^{13})R^{14}$; each $R^{13}$ and $R^{14}$ is independently hydrogen, alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl); $R^{15}$ is a straight or branched alkylene chain; and $R^{16}$ is alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl).

Of this subgroup of compounds, a preferred class of compounds is that class of compounds wherein $Z^1$ and $Z^2$ are each —O—; $R^1$ is hydrogen or —$OR^{13}$; $R^2$ is —$C(NH)NH_2$; $R^3$ is (1,2)-tetrahydropyrimidinyl (optionally substituted by methyl), (1,2)-imidazolyl (optionally substituted by methyl) or (1,2)-imidazolinyl (optionally substituted by methyl); $R^4$ is hydrogen; $R^5$ and $R^6$ are each halo; $R^7$ is —O—$(C(R^{10})(R^{11}))_n$—$R^{12}$ (where n is 1 to 6); $R^{10}$ is alkyl, —$R^{15}$—$N(R^{13})C(O)N(R^{13})R^{14}$, —$R^{15}$—$N(R^{13})C(NR^{13})N(R^{13})R^{14}$, —$R^{15}$—$N(R^{13})C(NR^{13})R^{16}$, —$R^{15}$—$C(O)OR^{13}$, —$R^{15}$—$C(O)N(R^{13})R^{14}$, —$R^{15}$—$C(R^{13})(C(O)OR^{13})_2$, —$R^{15}$—$N(R^{13})R^{14}$, —$R^{15}$—$SR^{13}$, —$R^{15}OR^{13}$, —$R^{15}$—$S(O)_2R^{16}$, —$R^{15}$—$OP(O)(OR^{13})_2$, or $R^{10}$ is aralkyl (optionally substituted by one or more substituents selected from the group consisting of halo, haloalkyl, hydroxy, or —$OP(O)(OR^{13})_2$), or $R^{10}$ is imidazolylalkyl, or indolylalkyl; $R^{11}$ is hydrogen or alkyl; $R_{12}$ is —$C(O)OR^{13}$ or —$C(O)N(R^{13})R^{14}$; each $R^{13}$ and $R^{14}$ is independently hydrogen or alkyl; $R^{15}$ is a straight or branched alkylene chain; and $R^{16}$ is alkyl or aryl.

Of this class of compounds, a preferred subclass of compounds is that subclass of compounds wherein $R^1$ is —$OR^{13}$; $R^3$ is (1,2)-imidazolyl (optionally substituted by methyl) or (1,2)-imidazolinyl (optionally substituted by methyl); $R^5$ and $R^6$ are both fluoro; $R^9$ is hydrogen or alkyl; $R^{10}$ is alkyl, —$R^{15}$—$N(R^{13})C(O)N(R^{13})R^{14}$, —$R^{15}$—$N(R^{13})C(NR^{13})R^{16}$, or —$R^{15}$—$N(R^{13})C(NR^{13})N(R^{13})R^{14}$; $R^{11}$ is hydrogen or alkyl; and $R^{12}$ is —$C(O)OR^{13}$.

Preferred compounds of this subclass of compound are selected from the following:

4-hydroxy-3-[(4-(1-ethoxycarbonyl-3-methylbutoxy)-6-(3-(1-methyl)imidazolin-2-yl)phenoxy-3,5-difluoropyridin-2-yl)oxy]benzamidine; and 4-hydroxy-3-[(4-(1-carboxy-3-methylbutoxy)-6-(3-(1-methyl)imidazolin-2-yl)phenoxy-3,5-difluoropyridin-2-yl)oxy]benzamidine.

Preparation of Compounds of The Invention

As a matter of convenience, the following description of the preparation of the compounds of the invention is directed to the preparation of compounds of formula (I) where A is —N=. It is understood, however, that similar synthetic processes may be used to prepare the compounds of formula (II), (III), (IV), (V), (VI), and (VII). It is also understood that in the following description, combinations of substituents and/or variables (e.g., $R^{10}$ and $R^{11}$) on the depicted formulae are permissible only if such combinations result in stable compounds.

A. Preparation of Compounds of Formulae (Ia) and (Ib)

Compounds of formulae (Ia) and (Ib) are compounds of the invention, as described above in the Summary of the Invention and may be prepared as illustrated below in Reaction Scheme 1, where X is halo; Y is bromo, chloro or iodo; $R^{13}$ is alkyl or aralkyl (optionally substituted by halo, alkyl, aryl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl); and $R^1$, $R^3$, $R^4$, $R^5$, $R^6$, $R^9$, $R^{10}$, and $R^{11}$ are as described above in the Summary of the Invention (except $R^{13}$ is not aryl in the description of $R^{10}$ and $R^{11}$):

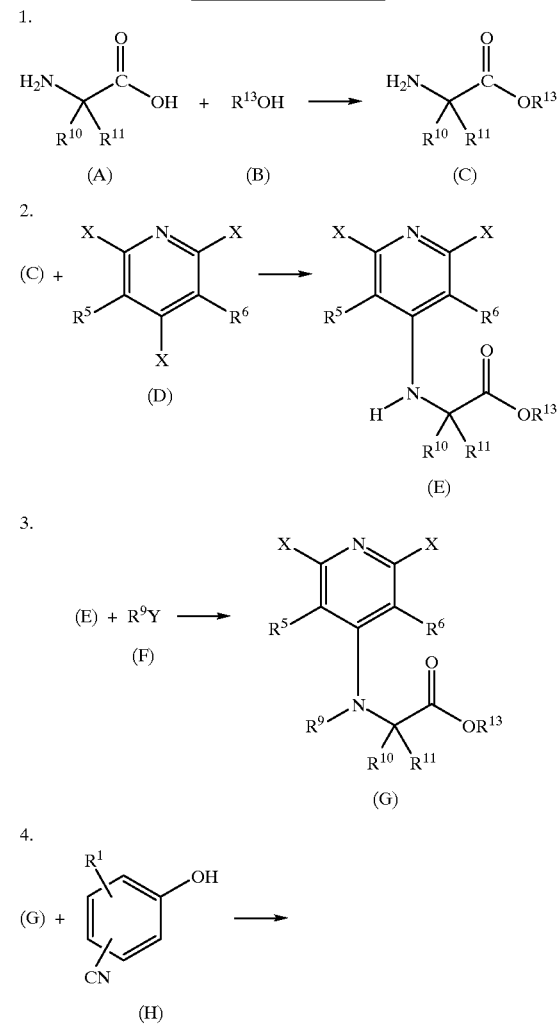

-continued

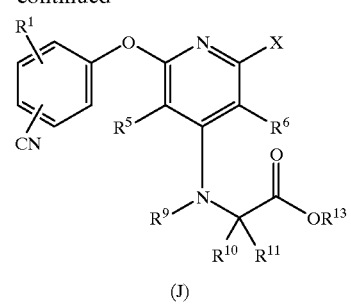

(J)

5.

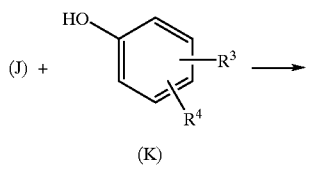

(J) + (K) →

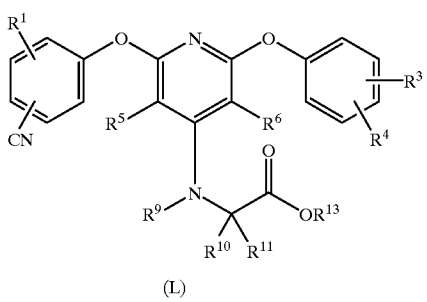

(L)

6.

(L) →

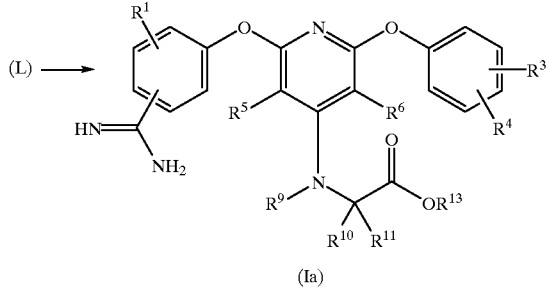

(Ia)

7.

(Ia) →

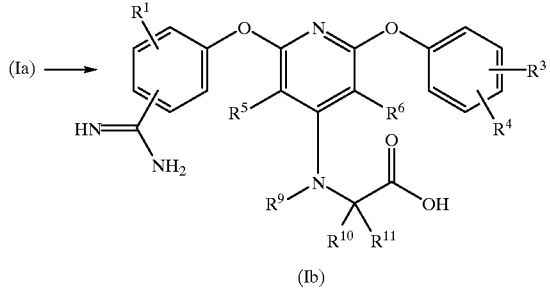

(Ib)

The amino acids of formula are commercially available, for example from Aldrich Chemical Co., Sigma Chemical Co., or ICN Biomedicals, Inc. The compounds of formulae (B), (D), (F), (H) and (K) are commercially available, for example, from Aldrich Chemical Co., or may be prepared according to methods known to those skilled in the art.

In general, the compounds of formulae (Ia) and (Ib) are prepared by first treating a compound of formula (A) with a compound of formula (B) under standard esterification conditions, for example, at temperatures of −100° C. to 50° C., preferably at ambient temperature, in the presence of a strong mineral acid, for example, hydrochloric acid (gas), to yield a compound of formula (C), which is isolated from the reaction mixture by standard techniques, such as in vacuo removal of solvent.

The resulting compound of formula (C) is then treated with a compound of formula (D) in an aprotic solvent, for example, DMSO, in the presence of a base, for example, triethylamine, at −20° C. to 50° C., preferably at ambient temperature, for about 20 to 40 hours. The compound of formula (E) is then isolated from the reaction mixture by standard techniques, such as extraction, filtration and in vacuo removal of solvent.

The resulting compound of formula (E) is then treated with a compound of formula (F) under standard alkylation conditions, for example, in an aprotic solvent, for example, acetonitrile, in the presence of a base, for example, sodium hydride, at ambient temperature for 1 to 24 hours, preferably for about 2 hours. The compound of formula (G) is then isolated from the reaction mixture standard techniques, such as extraction in vacuo removal of solvent and flash chromatography.

The resulting compound of formula (G) in an aprotic solvent, for example, acetonitrile, is treated with an equimolar molar amount of a compound of formula (H) in the presence of a base, for example, cesium carbonate, at temperatures between about 20° C. and 120° C., preferably at ambient temperature, for a period of time sufficient to complete the desired reaction as monitored by thin layer chromatography (TLC). The compound of formula (J) is then isolated from the reaction mixture by standard isolation techniques, such as extraction, in vacuo removal of solvent, and flash chromatography.

The resulting compound of formula (J) in an aprotic solvent, for example, DMSO, is then treated with an equimolar amount of a compound of formula (K) in the presence of a base, for example, cesium carbonate, at temperatures between about 20° C. and 120° C., preferably at about 35° C., for period of time sufficient to complete the desired reaction, for example, for about 13 hours. The reaction mixture is cooled to ambient temperature and the compound of formula (L) is then isolated from the reaction mixture through standard isolated techniques, such as extraction, in vacuo removal of solvent, and flash chromatography.

The resulting compound of formula (L) is dissolved in an anhydrous alkanol, preferably ethanol, and treated with an anhydrous mineral acid, preferably HCl, while maintaining the reaction temperatures between about -78° C. and ambient temperature for between 2 hours and 24 hours, allowing the temperature to rise to ambient temperature while monitoring for reaction completion, for example, through TLC. The solvent is removed in vacuo and the resulting residue is dissolved in fresh anhydrous alkanol, preferably ethanol, and then treated with anhydrous ammonia (gas) at temperatures from between ambient temperature and 100° C. for about 1 to about 5 hours, preferably for about 2 hours. The compound of formula (Ia) is then isolated from the reaction mixture by standard isolation techniques, for example, in vacuo removal of solvent and purification by high pressure liquid chromatography (HPLC).

Alternatively, instead of treating the resulting residue above with anhydrous ammonia, the resulting residue may be treated with a compound of the formula $NH_2OR^{13}$ to afford the corresponding compound of formula (Ia) wherein $R^2$ is $-C(NH)N(H)OR^{13}$.

The resulting compound of formula (Ia) is then hydrolyzed under acid conditions, for example, treatment with a strong mineral acid such as HCl, to produce the compound of formula (Ib). In addition, during this step, any compounds of formula (Ia) so produced which contain esters as a $R^1$, $R^3$, $R^4$, $R^5$, $R^6$, $R^{10}$, $R^{11}$, $R^{13}$, or $R^{14}$ substituent are hydrolyzed to compounds that contain the corresponding acid substituent.

In addition, compounds of formula (Ia) may be treated under standard transesterification conditions with an alcohol of the formula $R^{13}OH$ where $R^{13}$ is aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl) to produce compounds of the invention where $R^{13}$ is optionally substituted aryl.

Compounds of formula (Ia) wherein $R^3$ is —C(NH)NH$_2$ or —C(NH)N(H)OR$^{13}$ are produced from the corresponding cyano compounds in a similar manner as that described above for compound of formula (L).

In addition, compounds of formula (Ia) wherein $R^1$, $R^3$, $R^4$, $R^5$, $R^6$, $R^9$, $R^{10}$ or $R^{11}$ contains a —C(O)N($R^{13}$)$R^{14}$ group or a —C(O)OR$^{13}$ group (where each $R^{13}$ or $R^{14}$ is independently alkyl, optionally substituted aryl or optionally substituted aralkyl) may be hydrolyzed under acidic conditions to prepare corresponding compounds of the invention where $R^1$, $R^3$, $R^4$, $R^5$, $R^6$, $R^9$, $R^{10}$ or $R^{11}$ contains a —C(O)OH group.

In addition, compounds of formula (Ia) wherein $R^1$, $R^3$, $R^4$, $R^5$, $R^6$, $R^9$, $R^{10}$ or $R^{11}$, contains a —C(O)OR$^{13}$ group where $R^{13}$ is hydrogen, alkyl, optionally substituted aryl or optionally substituted aralkyl may be amidated under standard amidation conditions to form the corresponding compounds of formula (Ia) where $R^1$, $R^3$, $R^4$, $R^5$, $R^6$, $R^9$, $R^{10}$ or $R^{11}$ contains a —C(O)N($R^{13}$)$R^{14}$ group where $R^{13}$ and $R^{14}$ are independently hydrogen, alkyl, optionally substituted aryl or optionally substituted aralkyl.

In addition, compounds of formula (Ia) where $R^1$, $R^3$, $R^4$, $R^5$, $R^6$, or $R^{10}$ contains a nitro group may be reduced under standard conditions to produce the corresponding compounds of formula (Ia) where $R^1$, $R^3$, $R^4$, $R^5$, $R^6$, or $R^{10}$ contains an amino group, which can be treated with the appropriate alkylating agents to afford the corresponding compounds of formula (Ia) where $R^1$, $R^3$, $R^4$, $R^5$, $R^6$, or $R^{10}$ contains —N($R^{13}$)$R^{14}$ or —N($R^{13}$)C(O)$R^{14}$ where each $R^{13}$ and $R^{14}$ is independently hydrogen, alkyl, optionally substituted aryl or optionally substituted aralkyl.

Compounds of formula (Ia) may be further treated with the appropriate acid halide, preferably acid chloride, or with the appropriate acid anhydride or an equivalent, to yield compounds of the invention wherein $R^2$ is —C(NH)N(H)C(O)$R^{13}$ where $R^{13}$ is hydrogen, alkyl, optionally substituted aryl or optionally substituted aralkyl. Alternatively, compounds of formula (Ia) may further be treated with carbamoyl chlorides or their equivalents to yield compounds of the invention where $R^2$ is —C(NH)N(H)C(O)OR$^{16}$ where $R^{16}$ is described above in the Summary of the Invention.

Alternatively, compounds of formula (Ia) may be further treated with compounds of the formula $R^6$—S(O)$_2$-imidazole where $R^{16}$ is described in the Summary of the Invention in a polar solvent, such as methylene choride, at ambient temperature to afford compounds of the invention where $R^2$ is —C(NH)N(H)S(O)$_2R^{16}$.

Alternatively, compounds of formula (Ia) may be further treated with an appropriatly N—$R^{13}$-substituted phenylcarbamate in a polar solvent, preferably methylene chloride, at ambient temperature, for about 6 to 24 hours, preferably for about 12 hours, to afford compounds of the invention where $R^2$ is —C(NH)N(H)C(O)N(H)$R^{13}$.

In addition, if compounds of formula (A) are already substituted on the amino radical by $R^9$ subsitutents as described above in the Summary of the Invention, such compounds do not require the alkylation process of Step 3, as described above in the Reaction Scheme 1.

B. Preparation of Compounds of Formula (N)

Compounds of formula (N) are intermediates in the preparation of the compounds of the invention and may be prepared as illustrated below in Reaction Scheme 2, where X is halo; $R^{13}$ is alkyl or aralkyl (optionally substituted by halo, alkyl, aryl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl); and $R^5$, $R^6$, $R^{10}$ and $R^{11}$ are as described above in the Summary of the Invention (except $R^{13}$ is not aryl in the description of $R^{10}$ and $R^1$l):

REACTION SCHEME 2

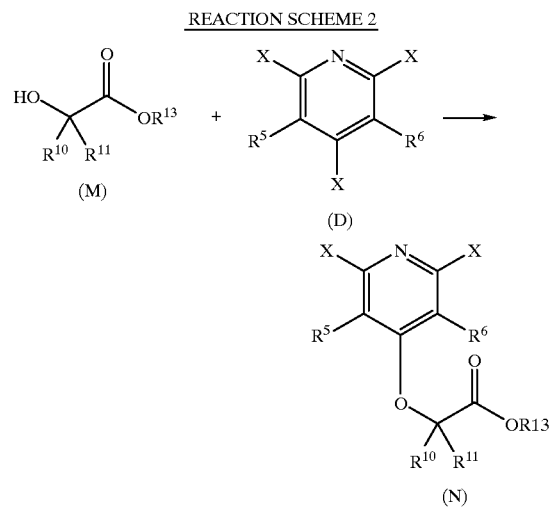

The hydroxy acids of formula (M) are commercially available, for example, from Aldrich Chemical Co., Sigma Chemical Co., or ICN Biomedicals, Inc., or may be prepared according to methods known to those skilled in the art. Compounds of formula (D) are commercially available, for example, from Aldrich Chemical Co., or may be prepared according to methods known to those skilled in the art.

In general, the compound of formula (N) is prepared by treating a compound of formula (M) in an aprotic solvent, such as DMF, with a compound of formula (D) in the presence of a base, for example, cesium carbonate, at temperatures at between about ambient temperature and 50° C., preferably at about 45° C. The reaction mixture is stirred at that temperature for about 24 hours to about 72 hours, preferably for about 72 hours. The compound of formula (N) is then isolated from the reaction mixture by standard isolation techniques, such as extraction, in vacuo removal of solvent, and flash chromatography.

The compound of formula (N) may then be treated in a manner similar to compound of formula (E) as described above in Reaction Scheme 1 to produce compounds of the invention, in e corresponding compounds where $R^{13}$ is hydrogen or aryl (through hydrolysis or transesterification).

C. Preparation of Compounds of Formula (Q)

Compounds of formula (Q) are intermediates in the preparation of the compounds of the invention and may be prepared as illustrated below in Reaction Scheme 3, where X is halo, and $R^1$, $R^3$, $R^4$, $R^9$, $R^{11}$, $R^{13}$ and $R^{14}$ are as described above in the Summary of the Invention, and $R^{17}$ is alkyl, aryl or aralkyl:

REACTION SCHEME 3

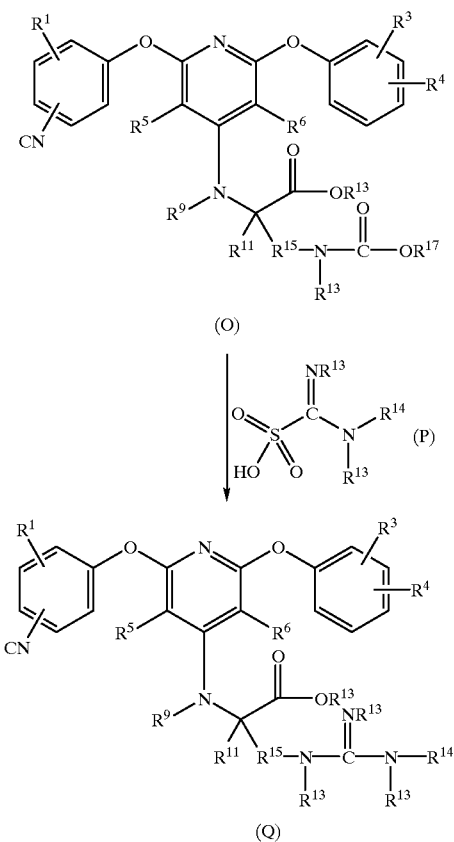

Compounds of formula (O) are prepared according to the methods described above in Reaction Scheme 1. Compounds of formula (P) are commercially available, for example, from Aldrich Chemical Co., or may be prepared according to methods known to those of ordinary skill in the art. 5 In general, compounds of formula (Q) are prepared by first dissolving a compound of formula (O) in an aprotic solvent, for example, methylene chloride, in the presence of an organic acid, for example, trifluoroacetic acid (TFA), and stirring the resulting solution at ambient temperature for about 1 hour to about 10 hours, preferably for about 1.5 hours. The solvent is then removed and the resulting residue is dissolved in an aqueous solution of an alkanol, preferably methanol/water, in the presence of a base, for example, potassium carbonate, until a pH of 10 to 12, preferably pH 11, is reached. The resulting solution is then treated with the compound of formula (P), and the resulting mixture is stirred at ambient temperature until completion of reaction, for example, by analyzing an aliquot of the mixture on HPLC for desired products. The compound of formula (Q) is then isolated from the reaction mixture by standard isolation techniques, such as extraction, filtration, in vacuo removal of solvent, and chromatography.

Other amidinyl acids of formula (P) may be used in this reaction scheme to produce corresponding compounds of formula (Q).

Compounds of formula (Q) may then be treated in a manner similar to the compound of formula (L) in Reaction Scheme 1 above to produce the corresponding compound of the invention.

D. Preparation of Compounds of Formula (Ic) and (Id)

Compounds of formula (Ic) and (Id) are compounds of the invention and may be prepared as illustrated below in Reaction Scheme 4, where X is halo, and $R^1$, $R^3$, $R^4$, $R^9$, $R^{11}$, $R^{13}$, $R^{14}$, $R^{15}$ and $R^{16}$ are as described above in the Summary of the Invention, and $R^{17}$ is alkyl, aryl or aralkyl:

REACTION SCHEME 3

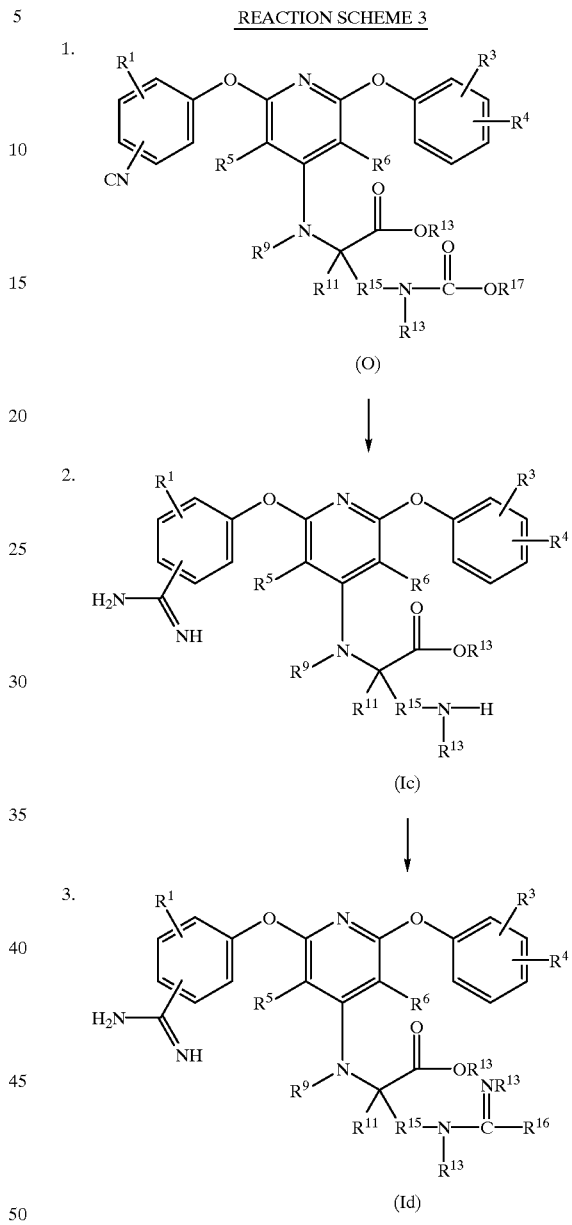

Compounds of formula (O) are prepared according to the methods described above in Reaction Scheme 1.

In general, compounds of formula (Ic) and (Id) are prepared by first dissolving a compound of formula (O) in an aprotic/alkanol solvent, for example, ethanol/methylene chloride, and then reducing the solution temperature to about −20° C. to 0° C., preferably to about −10° C., and then treating the solution to a mineral acid, preferably HCl, for about 15 minutes to an hour, preferably for about 15 minutes. The reaction mixture is then stirred at ambient temperature for about 10 hours to 20 hours, preferably for 20 hours. The volatile solvents are then removed in vacuo, and the resulting residue in then dissolved in an alcohol, preferably absolute ethanol. The resulting solution is then cooled from about −20° C. to about 0° C., preferably to about −10° C., and treated with anhydrous ammonia (gas) at ambient temperature for about 15 minutes to about 1 hour, preferably for about 15 minutes. The resulting mixture is then heated to reflux for about 1 hour to 3 hours, preferably for about 2 hours, and then cooled to ambient temperature and concentrated. The resulting residue is then dissolved in an aqueous mineral acid, for example aqueous HCl, and heated to reflux temperature for about 2 hours to 4 hours, preferably for about 4 hours. The compound of formula (Ic) is then isolated from the reaction mixture by standard isolation techniques, such as purification by HPLC.

The compound of formula (Ic) may then be dissolved in an aqueous alcoholic solvent, for example, methanol/water. To the resulting solution was added an alkyl acetimidate, preferably ethyl acetimidate, in the presence of a strong organic base, such as potassium carbonate. The resulting reaction mixture is stirred for about 1 hour to about 3 hours, preferably for 1 hour, at ambient temperature. The compound of formula (Id) is then isolated from the reaction mixture by standard isolation techniques, such as filtration and chromatography.

In addition, all compounds of the invention that exist in free base form or free acid form may be converted to their pharmaceutically acceptable salts by treatment with the appropriate inorganic or organic acid, or by the appropriate inorganic or organic base. Salts of the compounds of the invention can also be converted to the free base form or to the free acid form or to another salt.

The following specific preparations and examples are provided as a guide to assist in the practice of the invention, and are not intended as a limitation on the scope of the invention.

PREPARATION 1

Compounds of Formula (C)

A. A solution of 2-aminoisobutyric acid (3.3 g, 32 mmol) in absolute ethanol (100 mL) was cooled to −78° C. and HCl(g) bubbled in for 10 minutes. The flask was sealed with a septum and stirred at ambient temperature. After 14 hours the mixture was concentrated in vacuo to afford 5.3 g (99% yield) of ethyl 2-aminoisobutyrate as a white solid; NMR (CDCl$_3$) 8.9 (br s, 3), 4.1 (q, 2), 1.7 (s, 6), 1.3 (t, 3) ppm.

B. In a similar manner, the following compound was made:
ethyl 2-N-methylaminopropionate.

C. In a similar manner, the following compounds are made:
ethyl 2-methyl-2-aminopropionate;
ethyl 2-methylethyl-2-aminopropionate;
ethyl 2-(2-methylpropyl)-2-aminopropionate;
ethyl 2-(1-methylpropyl)-2-aminopropionate;
ethyl 2-(hydroxymethyl)-2-aminopropionate;
ethyl 2-(1-hydroxyethyl)-2-aminopropionate;
ethyl 2-(mercaptomethyl)-2-aminopropionate;
--ethyl 2-(2-methylthioethyl)-2-aminopropionate;
ethyl 2-(carboxymethyl)-2-aminopropionate;
ethyl 2-(aminocarbonylmethyl)-2-aminopropionate;
ethyl 2-(2-carboxyethyl)-2-aminopropionate;
ethyl 2-(2-aminocarbonylethyl)-2-aminopropionate;
ethyl 2-(3-guanidinopropyl)-2-aminopropionate;
ethyl 2-(4-guanidinobutyl)-2-aminopropionate;
ethyl 2-(4-aminobutyl)-2-aminopropionate;
ethyl 2-(4-amino-3-hydroxybutyl)-2-aminopropionate;
methyl 2-(4-(N-tert-butoxycarbonylamino)butyl)-2-aminopropionate;
methyl 2-(imidazol-4-ylmethyl)-2-aminopropionate;
methyl 2-(phenylmethyl)-2-aminopropionate;
methyl 2-((4-hydroxyphenyl)methyl)-2-aminopropionate;
methyl 2-(indol-3-ylmethyl)-2-aminopropionate;
methyl 2-(2-mercaptoethyl)-2-aminopropionate;
methyl 2-(2-hydroxyethyl)-2-aminopropionate;
methyl 2-(3-aminopropyl)-2-aminopropionate;
methyl 2-(3-ureidopropyl)-2-aminopropionate; and
methyl 2-(2,2-dicarboxyethyl)-2-aminopropionate.

PREPARATION 2

Compounds of Formula (E)

A. To a solution of ethyl 2-aminoisobutyrate (2.0 g, 12 mmol) in dry DMSO (125 mL) was added pentafluoropyridine (1.6 mL, 2.4 g, 14.4 mmol) and triethylamine (8.3 mL, 6.1 g, 60 mmol). The resultant mixture was stirred at ambient temperature for 40 hours then poured into 300 mL of water and 300 mL of ethyl acetate. The aqueous layer was separated and extracted with another 100 mL of ethyl acetate. The combined organic extracts were washed with water (250 mL) then brine (250 mL), dried over MgSO$_4$, filtered, and concentrated in vacuo to afford 3.5 g (92% yield) of 4-N-(1-ethoxycarbonyl-1-methylethyl)amino-2,3,5,6-tetrafluoropyridine as a crystalline solid: NMR (CDCl$_3$) 5.0 (br s, 1), 4.2 (q, 2), 1.7 (s, 6), 1.3 (t, 3) ppm.

B. In a similar manner, the following compounds were made:
4-N-(1-tert-butoxycarbonyl-5-(N-tert-butoxycarbonyl)aminopent-1-yl)amino-2,3,5,6-tetrafluoropyridine; and
4-N-methyl-N-(1-ethoxycarbonylethyl)amino-2,3,5,6-tetrafluoropyridine.

C. In a similar manner, the following compounds are made:
4-N-(1-ethoxycarbonyl-3-methylbutyl)amino-2,3,5,6-tetrafluoropyridine;
4-N-(1-ethoxycarbonyl-2-methylpropyl)amino-2,3,5,6-tetrafluoropyridine;
4-N-(1-ethoxycarbonyl-2-methylbutyl)amino-2,3,5,6-tetrafluoropyridine;
4-N-(1-ethoxycarbonyl-2-mercaptoethyl)amino-2,3,5,6-tetrafluoropyridine;
4-N-(1-ethoxycarbonyl-3-methylthiopropyl)amino-2,3,5,6-tetrafluoropyridine;
4-N-(1-ethoxycarbonyl-2-hydroxyethyl)amino-2,3,5,6-tetrafluoropyridine;
4-N-(1-ethoxycarbonyl-2-hydroxypropyl)amino-2,3,5,6-tetrafluoropyridine;
4-N-(1-ethoxycarbonyl-2-carboxyethyl)amino-2,3,5,6-tetrafluoropyridine;
4-N-(1-ethoxycarbonyl-2-aminocarbonylethyl)amino-2,3,5,6-tetrafluoropyridine;
4-N-(1-ethoxycarbonyl-3-carboxypropyl)amino-2,3,5,6-tetrafluoropyridine;
4-N-(1-ethoxycarbonyl-3-aminocarbonylpropyl)amino-2,3,5,6-tetrafluoropyridine;
4-N-(1-ethoxycarbonyl-2-imidazol4-ylethyl)amino-2,3,5,6-tetrafluoropyridine;
4-N-(1-ethoxycarbonyl-2-phenylmethylethyl)amino-2,3,5,6-tetrafluoropyridine;
4-N-(1-ethoxycarbonyl-2-indol-3-ylethyl)amino-2,3,5,6-tetrafluoropyridine;
4-N-(1-ethoxycarbonyl-4-guanidinobutyl)amino-2,3,5,6-tetrafluoropyridine; and
4-N-(1-ethoxycarbonyl-4-aminobutyl)amino-2,3,5,6-tetrafluoropyridine.

PREPARATION 3

Compounds of Formula (G)

A. To a solution of 4-N-(1-ethoxycarbonyl-1-methylethyl)amino-2,3,5,6-tetrafluoropyridine (3.1 g, 9.8 mmol) in acetonitrile (70 mL) was added sodium hydride (0.8 g, 20 mmol, 60% dispersion in mineral oil). After gas evolution ceased, iodomethane (1.25 mL, 2.8 g, 20 mmol) was added and the resultant mixture was stirred at ambient temperature for 2 hours. The mixture was then poured into 200 mL of water and 200 mL of ethyl acetate. The aqueous layer was separated and extracted with another 100 mL of ethyl acetate. The combined organic extracts were dried over MgSO$_4$, filtered, and concentrated in vacuo to afford a brown oil. Purification by flash chromatography on silica gel afforded 2.2 g (68% yield) of 4-N-methyl-N-(1-ethoxycarbonyl-1-methylethyl)amino-2,3,5,6-tetrafluoropyridine as a clear, colorless liquid: NMR (CDCl$_3$) 4.2 (q, 2), 3.1 (s, 3), 1.6 (s, 6), 1.3 (t, 3) ppm.

B. In a similar manner, the following compounds are made:

4-N-ethyl-N-(1-ethoxycarbonyl-1-methylethyl)amino-2,3,5,6-tetrafluoropyridine;
4-N-propyl-N-(1-ethoxycarbonyl-1-methylethyl)amino-2,3,5,6-tetrafluoropyridine;
4-N-butyl-N-(1-ethoxycarbonyl-1-methylethyl)amino-2,3,5,6-tetrafluoropyridine;
4-N-phenyl-N-(1-ethoxycarbonyl-1-methylethyl)amino-2,3,5,6-tetrafluoropyridine;
4-N-benzyl-N-(1-ethoxycarbonyl-1-methylethyl)amino-2,3,5,6-tetrafluoropyridine;
4-N-(3-ethoxycarbonyl)propyl-N-(1-ethoxycarbonyl-1-methylethyl)amino-2,3,5,6-tetrafluoropyridine;
4-N-(4-dimethylaminocarbonyl)butyl-N-(1-ethoxycarbonyl-1-methylethyl)amino-2,3,5,6-tetrafluoropyridine;
4-N-(4-dimethylaminobutyl)-N-(1-ethoxycarbonyl-1-methylethyl)amino-2,3,5,6-tetrafluoropyridine;
4-N-propyl-N-(1-ethoxycarbonyl-3-methylbutyl)amino-2,3,5,6-tetrafluoropyridine;
4-N-methyl-N-(1-ethoxycarbonyl-2-methylpropyl)amino-2,3,5,6-tetrafluoropyridine;
4-N-methyl-N-(1-ethoxycarbonyl-2-methylbutyl)amino-2,3,5,6-tetrafluoropyridine;
4-N-methyl-N-(1-ethoxycarbonyl-2-mercaptoethyl)amino-2,3,5,6-tetrafluoropyridine;
4-N-methyl-N-(1-ethoxycarbonyl-3-methylthiopropyl)amino-2,3,5,6-tetrafluoropyridine;
4-N-methyl-N-(1-ethoxycarbonyl-2-hydroxyethyl)amino-2,3,5,6-tetrafluoropyridine;
4-N-methyl-N-(1-ethoxycarbonyl-2-hydroxypropyl)amino-2,3,5,6-tetrafluoropyridine;
4-N-methyl-N-(1-ethoxycarbonyl-2-carboxyethyl)amino-2,3,5,6-tetrafluoropyridine;
4-N-methyl-N-(1-ethoxycarbonyl-2-aminocarbonylethyl)amino-2,3,5,6-tetrafluoropyridine;
4-N-methyl-N-(1-ethoxycarbonyl-3-carboxypropyl)amino-2,3,5,6-tetrafluoropyridine;
4-N-methyl-N-(1-ethoxycarbonyl-3-aminocarbonylpropyl)amino-2,3,5,6-tetrafluoropyridine;
4-N-methyl-N-(1-ethoxycarbonyl-2-imidazol-4-ylethyl)amino-2,3,5,6-tetrafluoropyridine;
4-N-methyl-N-(1-ethoxycarbonyl-2-phenylmethylethyl)amino-2,3,5,6-tetrafluoropyridine;
4-N-methyl-N-(1-ethoxycarbonyl-2-indol-3-ylethyl)amino-2,3,5,6-tetrafluoropyridine;
4-N-methyl-N-(1-ethoxycarbonyl-4-guanidinobutyl)amino-2,3,5,6-tetrafluoropyridine; and
4-N-methyl-N-(1-ethoxycarbonyl-4-aminobutyl)amino-2,3,5,6-tetrafluoropyridine.

PREPARATION 4

Compounds of Formula (J)

A. To a solution of 4-[N-methyl-N-(1-ethoxycarbonyl-1-methylethyl)amino]-2,3,5,6-tetrafluoropyridine (2.2 g, 6.6 mmol) in acetonitrile (60 mL) was added 2-benzyloxy-5-cyanophenol (1.5 g, 6.6 mmol) and cesium carbonate (2.8 g, 8.6 mmol). The resultant mixture was stirred at 40° C. for 2 days. The mixture was then cooled to ambient temperature and poured into 200 mL of 0.5 M aqueous KOH solution and 200 mL of ethyl acetate. The aqueous layer was separated and extracted with another 100 mL of ethyl acetate. The combined organic extracts were washed with 0.5 M aqueous KOH solution (200 mL) then brine (200 mL), dried over MgSO$_4$, filtered, and concentrated in vacuo to afford a yellow oil which solidified upon standing. Recrystallization from 30% ethyl acetate/hexanes afforded 2.4 g (68% yield) of 4-benzyloxy-3-[(4-(N-methyl-N-(1-ethoxycarbonyl-1-methylethyl)amino)-3,5,6-trifluoropyridin-2-yl)oxy]benzonitrile as a white, crystalline solid: NMR (CDCl$_3$) 7.6–7.1 (m, 8), 5.2 (s, 2), 4.2 (q, 2), 3.1 (s, 3), 1.6 (s, 6), 1.3 (t, 3) ppm.

B. In a similar manner, the following compounds were made:

4-benzyloxy-3-[(4-(N-(1-tert-butoxycarbonyl-5-(N-tert-butoxycarbonylamino)pentyl)amino)-3,5,6-trifluoropyridin-2-yl)oxy]benzonitrile; and
4-benzyloxy-3-[(4-(N-methyl-N-(1-ethoxycarbonyl)ethylamino)-3,5,6-trifluoropyridin-2-yl)oxy]benzonitrile.

C. In a similar manner, the following compounds are made:

4-benzyloxy-3-[(4-(N-ethyl-N-(1-ethoxycarbonyl-1-methylethyl)amino)-3,5,6-trifluoropyridin-2-yl)oxy]benzonitrile;
4-benzyloxy-3-[(4-(N-propyl-N-(1-ethoxycarbonyl-1-methylethyl)amino)-3,5,6-trifluoropyridin-2-yl)oxy]benzonitrile;
4-benzyloxy-3-[(4-(N-butyl-N-(1-ethoxycarbonyl-1-methylethyl)amino)-3,5,6-trifluoropyridin-2-yl)oxy]benzonitrile;
4-benzyloxy-3-[(4-(N-phenyl-N-(1-ethoxycarbonyl-1-methylethyl)amino)-3,5,6-trifluoropyridin-2-yl)oxy]benzonitrile;
4-benzyloxy-3-[(4-(N-benzyl-N-(1-ethoxycarbonyl-1-methylethyl)amino)-3,5,6-trifluoropyridin-2-yl)oxy]benzonitrile;
4-benzyloxy-3-[(4-(N-(3-ethoxycarbonylpropyl)-N-(1-ethoxycarbonyl-1-methylethyl)amino)-3,5,6-trifluoropyridin-2-yl)oxy]benzonitrile;
4-benzyloxy-3-[(4-(N-(4-aminocarbonylbutyl)-N-(1-ethoxycarbonyl-1-methylethyl)amino)-3,5,6-trifluoropyridin-2-yl)oxy]benzonitrile;
4-benzyloxy-3-[(4-(N-(4-aminobutyl)-N-(1-ethoxycarbonyl-1-methylethyl)amino)-3,5,6-trifluoropyridin-2-yl)oxy]benzonitrile;
4-benzyloxy-3-[(4-(N-propyl-N-(1-ethoxycarbonyl-3-methylbutyl)amino)-3,5,6-trifluoropyridin-2-yl)oxy]benzonitrile;
4-benzyloxy-3-[(4-(N-methyl-N-(1-ethoxycarbonyl-2-methylpropyl)amino)-3,5,6-trifluoropyridin-2-yl)oxy]benzonitrile;
4-benzyloxy-3-[(4-(N-methyl-N-(1-ethoxycarbonyl-2-methylbutyl)amino)-3,5,6-trifluoropyridin-2-yl)oxy]benzonitrile;
4-benzyloxy-3-[(4-(N-methyl-N-(1-ethoxycarbonyl-2-mercaptoethyl)amino)-3,5,6-trifluoropyridin-2-yl)oxy]benzonitrile;
4-benzyloxy-3-[(4-(N-methyl-N-(1-ethoxycarbonyl-3-methylthiopropyl)amino)-3,5,6-trifluoropyridin-2-yl)oxy] benzonitrile;
4-benzyloxy-3-[(4-(N-methyl-N-(1-ethoxycarbonyl-2-hydroxyethyl)amino)-3,5,6-trifluoropyridin-2-yl)oxy]benzonitrile;

4-benzyloxy-3-[(4-(N-methyl-N-(1-ethoxycarbonyl-2-hydroxypropyl)amino)-3,5,6-trifluoropyridin-2-yl)oxy]benzonitrile;
4-benzyloxy-3-[(4-(N-methyl-N-(1-ethoxycarbonyl-2-carboxyethyl)amino)-3,5,6-trifluoropyridin-2-yl)oxy]benzonitrile;
4-benzyloxy-3-[(4-(N-methyl-N-(1-ethoxycarbonyl-2-carboxyethyl)amino)-3,5,6-trifluoropyridin-2-yl)oxy]benzonitrile;
4-benzyloxy-3-[(4-(N-methyl-N-(1-ethoxycarbonyl-2-aminocarbonylethyl)amino)-3,5,6-trifluoropyridin-2-yl)oxy]benzonitrile;
4-benzyloxy-3-[(4-(N-methyl-N-(1-ethoxycarbonyl-3-carboxylpropyl)amino)-3,5,6-trifluoropyridin-2-yl)oxy]benzonitrile;
4-benzyloxy-3-[(4-(N-methyl-N-(1-ethoxycarbonyl-3-aminocarbonylpropyl)amino)-3,5,6-trifluoropyridin-2-yl)oxy]benzonitrile;
4-benzyloxy-3-[(4-(N-methyl-N-(5-ethoxycarbonyl-2-imidazol-4-ylethyl)amino)-3,5,6-trifluoropyridin-2-yl)oxy]benzonitrile;
4-benzyloxy-3-[(4-(N-methyl-N-(1-ethoxycarbonyl-2-phenylmethylethyl)amino)-3,5,6-trifluoropyridin-2-yl)oxy]benzonitrile;
4-benzyloxy-3-[(4-(N-methyl-N-(1-ethoxycarbonyl-2-indol-3-ylethyl)amino)-3,5,6-trifluoropyridin-2-yl)oxy]benzonitrile;
4-benzyloxy-3-[(4-(N-methyl-N-(1-ethoxycarbonyl4-guanidinobutyl)amino)-3,5,6-trifluoropyridin-2-yl)oxy]benzonitrile;
4-benzyloxy-3-[(4-(1-ethoxycarbonyl-4-guanidinobutoxy)-3,5,6-trifluoropyridin-2-yl)oxy]benzonitrile;
4-benzyloxy-3-[(4-(1-ethoxycarbonyl-1-methylethyoxy)-3,5,6-trifluoropyridin-2-yl)oxy]benzonitrile;
4-benzyloxy-3-[(4-(1-ethoxycarbonyl-1-methylethoxy)-3,5,6-trifluoropyridin-2-yl)oxy]benzonitrile;
4-benzyloxy-3-[(4-(1-ethoxycarbonyl-1-methylethoxy)-3,5,6-trifluoropyrid in-2-yl)oxy]benzonitrile;
4-benzyloxy-3-[(4-(1-ethoxycarbonyl-1-methylethoxy)-3,5,6-trifluoropyridin-2-yl)oxy]benzonitrile;
4-benzyloxy-3-[(4-(1-ethoxycarbonyl-1-methylethoxy)-3,5,6-trifluoropyridin-2-yl)oxy]benzonitrile;
4-benzyloxy-3-[(4-(1-ethoxycarbonyl-1-methylethoxy)-3,5,6-trifluoropyridin-2-yl)oxy]benzonitrile;
4-benzyloxy-3-[(4-(1-ethoxycarbonyl-1-methylethyoxy)amino)-3,5,6-trifluoropyridin-2-yl)oxy]benzonitrile;
4-benzyloxy-3-[(4-(1-ethoxycarbonyl-1-methylethoxy)-3,5,6-trifluoropyridin-2-yl)oxy]benzonitrile;
4-benzyloxy-3-[(4-(1-ethoxycarbonyl-3-methylbutoxy)-3,5,6-trifluoropyridin-2-yl)oxy]benzonitrile;
4-benzyloxy-3-[(4-(1-ethoxycarbonyl-2-methylpropoxy)-3,5,6-trifluoropyridin-2-yl)oxy]benzonitrile;
4-benzyloxy-3-[(4-(1-ethoxycarbonyl-2-methylbutoxy)-3,5,6-trifluoropyridin-2-yl)oxy]benzonitrile;
4-benzyloxy-3-[(4-(1-ethoxycarbonyl-2-mercaptoethoxy)-3,5,6-trifluoropyridin-2-yl)oxy]benzonitrile;
4-benzyloxy-3-[(4-(1-ethoxycarbonyl-3-methylthiopropoxy)-3,5,6-trifluoropyridin-2-yl)oxy]benzonitrile;
4-benzyloxy-3-[(4-(1-ethoxycarbonyl-2-hydroxyethoxy)-3,5,6-trifluoropyridin-2-yl)oxy]benzonitrile;
4-benzyloxy-3-[(4-(1-ethoxycarbonyl-2-hydroxypropoxy)-3,5,6-trifluoropyridin-2-yl)oxy]benzonitrile;
4-benzyloxy-3-[(4-(1-ethoxycarbonyl-2-carboxyethoxy)-3,5,6-trifluoropyridin-2-yl)oxy]benzonitrile;
4-benzyloxy-3-[(4-(1-ethoxycarbonyl-2-carboxyethoxy)-3,5,6-trifluoropyridin-2-yl)oxy]benzonitrile;
4-benzyloxy-3-[(4-(1-ethoxycarbonyl-2-aminocarbonylethoxy)-3,5,6-trifluoropyridin-2-yl)oxy]benzonitrile;
4-benzyloxy-3-[(4-(1-ethoxycarbonyl-3-carboxylpropoxy)-3,5,6-trifluoropyridin-2-yl)oxy]benzonitrile;
4-benzyloxy-3-[(4-(1-ethoxycarbonyl-3-aminocarbonylpropoxy)-3,5,6-trifluoropyridin-2-yl)oxy]benzonitrile;
4-benzyloxy-3-[(4-(1-ethoxycarbonyl-2-imidazol-4-ylethoxy)-3,5,6-trifluoropyridin-2-yl)oxy]benzonitrile;
4-benzyloxy-3-[(4-(1-ethoxycarbonyl-2-phenylmethylethoxy)-3,5,6-trifluoropyridin-2-yl)oxy]benzonitrile;
4-benzyloxy-3-[(4-(1-ethoxycarbonyl-2-indol-3-ylethoxy)-3,5,6-trifluoropyridin-2-yl)oxy]benzonitrile;
4-benzyloxy-3-[(4-(1-ethoxycarbonyl-4-guanidinobutoxy)-3,5,6-trifluoropyridin-2-yl)oxy]benzonitrile; and
4-benzyloxy-3-[(4-(1-ethoxycarbonyl-4-guanidinobutoxy)-3,5,6-trifluoropyridin-2-yl)oxy]benzonitrile.

PREPARATION 5

Compounds of Formula (L)

A. To a solution of 4-benzyloxy-3-[(4-(N-methyl-N-(1-ethoxycarbonyl-1-methylethyl)amino)-3,5,6-trifluoropyridin-2-yl)oxy]benzonitrile (2.4 g, 4.5 mmol) in DMSO (50 mL) was added 3-((1-methyl)imidazolin-2-yl)phenol (0.8 g, 4.5 mmol) and cesium carbonate (1.9 g, 5.8 mmol). The resultant mixture was stirred at 35° C. After 13 hours, the mixture was then cooled to ambient temperature and poured into 200 mL of water and 200 mL of ethyl acetate. The aqueous layer was separated and extracted with 100 mL of ethyl acetate. The combined organic extracts were washed with 0.5 M aqueous KOH solution (200 mL) then brine (200 mL), dried over $MgSO_4$, filtered, and concentrated in vacuo to afford 4-benzyloxy-3-[(4-(N-methyl-N-(1-ethoxycarbonyl-1-methylethyl)amino)-6-(3-(1-methylimidazolin-2-yl)phenoxy)-3,5-difluoropyridin-2-yl)-oxy]benzonitrile as a solid foam: NMR ($CDCl_3$) 7.4–7.0 (m, 12), 5.0 (s, 2), 4.2 (q, 2), 3.9 (t, 2), 3.5 (t, 2), 3.1 (s, 3), 2.8 (s, 3), 1.6 (s, 6), 1.3 (t, 3) ppm.

B. In a similar manner, the following compounds were made:

4-benzyloxy-3-[(4-(N-(1-tert-butoxycarbonyl-5-(N-tert-butoxycarbonyl)aminopent-1-yl)amino)-6-(3-(1-methylimidazol-2-yl)phenoxy)-3,5-difluoropyridin-2-yl)oxy]-benzonitrile;
4-benzyloxy-3-[(4-(N-(1-tert-butoxycarbonyl-5-(N-tert-butoxycarbonyl)aminopent-1-yl)amino)-6-(3-(1-methylimidazolin-2-yl)phenoxy)-3,5-difluoropyridin-2-yl)oxy]benzonitrile; and
4-benzyloxy-3-[(4-(N-methyl-N-(1-methoxycarbonyl)ethyl-amino)-6-(3-(1-methylimidazolin-2-yl)phenoxy)-3,5-difluoropyridin-2-yl)oxy]benzonitrile.

C. In a similar manner, the following compounds are made:

4-benzyloxy-3-[(4-(N-ethyl-N-(1-ethoxycarbonyl-1-methylethyl)amino)-6-(3-(1-methylimidazol-2-yl)phenoxy)-3,5-difluoropyridin-2-yl)oxy]benzonitrile;
4-benzyloxy-3-[(4-(N-propyl-N-(1-ethoxycarbonyl-1-methylethyl)amino)-6-(3-(1-methylimidazol-2-yl)phenoxy)-3,5-difluoropyridin-2-yl)oxy]benzonitrile;
4-benzyloxy-3-[(4-(N-butyl-N-(1-ethoxycarbonyl-1-methylethyl)amino)-6-(3-(1-methylimidazol-2-yl)phenoxy)-3,5-difluoropyridin-2-yl)oxy]benzonitrile;
4-benzyloxy-3-[(4-(N-phenyl-N-(1-ethoxycarbonyl-1-methylethyl)amino)-6-(3-(1-methylimidazol-2-yl)phenoxy)-3,5-difluoropyridin-2-yl)oxy]benzonitrile;

4-benzyloxy-3-[(4-(N-benzyl-N-(1-ethoxycarbonyl-1-methylethyl)amino)-6-(3-(1-methylimidazol-2-yl)phenoxy)-3,5-difluoropyridin-2-yl)oxy]benzonitrile;

4-benzyloxy-3-[(4-(N-(3-ethoxycarbonylpropyl)-N-(1-ethoxycarbonyl-1-methylethyl)amino)-6-(3-(1-methylimidazolin-2-yl)phenoxy)-3,5-difluoropyridin-2-yl)oxy]benzonitrile;

4-benzyloxy-3-[(4-(N-(4-aminocarbonylbutyl)-N-(1-ethoxycarbonyl-1-methylethyl)amino)-6-(3-(1-methylimidazolin-2-yl)phenoxy)-3,5-difluoropyridin-2-yl)oxy]benzonitrile;

4-benzyloxy-3-[(4-(N-(4-aminobutyl)-N-(1-ethoxycarbonyl-1-methylethyl)amino)-6-(3-(1-methylimidazol-2-yl)phenoxy)-3,5-difluoropyridin-2-yl)oxy]benzonitrile;

4-benzyloxy-3-[(4-(N-propyl-N-(1-ethoxycarbonyl-3-methylbutyl)amino)-6-(3-(1-methylimidazol-2-yl)phenoxy)-3,5-difluoropyridin-2-yl)oxy]benzonitrile;

4-benzyloxy-3-[(4-(N-methyl-N-(1-ethoxycarbonyl-2-methylpropyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-2-methylbutyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-2-mercaptoethyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-3-methylthiopropyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-2-hydroxyethyl)amino)-6-(3-(1-methylimidazol-2-yl)phenoxy)-3,5-difluoropyridin-2-yl)oxy]benzonitrile;

4-benzyloxy-3-[(4-(N-methyl-N-(1-ethoxycarbonyl-2-hydroxypropyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-2-carboxyethyl)amino)-6-(3-(1-methylimidazol-2-yl)phenoxy)-3,5-difluoropyridin-2-yl)oxy]benzonitrile;

4-benzyloxy-3-[(4-(N-methyl-N-(1-ethoxycarbonyl-2-carboxyethyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-2-aminocarbonylethyl)amino)-6-(3-(1-methylimidazol-2-yl)phenoxy)-3,5-difluoropyridin-2-yl)oxy]benzonitrile;

4-benzyloxy-3-[(4-(N-methyl-N-(1-ethoxycarbonyl-3-carboxylpropyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-3-aminocarbonylpropyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-2-imidazol-4-ylethyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-2-phenylmethylethyl)amino)-6-(3-(1-methylimidazol-2-yl)phenoxy)-3,5-difluoropyridin-2-yl)oxy]benzonitrile;

4-benzyloxy-3-[(4-(N-methyl-N-(1-ethoxycarbonyl-2-indol-3-ylethyl)amino)-6-(3-(1-methylimidazol-2-yl)phenoxy)-3,5-difluoropyridin-2-yl)oxy]benzonitrile;

4-benzyloxy-3-[(4-(N-methyl-N-(1-ethoxycarbonyl-4-guanidinobutyl)amino)-6-(3-(1-methylimidazolin-2-yl)phenoxy)-3,5-difluoropyridin-2-yl)oxy]benzonitrile;

4-benzyloxy-3-[(4-(N-methyl-N-(1-ethoxycarbonyl-4-guanidinobutyl)amino)-6-(3-(1-methylimidazol-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-1-methylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-3-methylbutoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-2-methylpropoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-2-methylbutoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-2-mercaptoethoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-3-methylthiopropoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-2-hydroxyethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-2-hydroxypropoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-2-carboxyethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-2-carboxyethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-2-aminocarbonylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-3-carboxylpropoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-3-aminocarbonylpropoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-2-imidazol4-ylethoxy)-6-(3-(1-methylimidazolin-2-yl)phenoxy)-3,5-difluoropyridin-2-yl)oxy]benzonitrile;

4-benzyloxy-3-[(4-(1-ethoxycarbonyl-2-phenylmethylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-2-indol-3-ylethoxy)-6-(3-(1-methylimidazol-2-yl)phenoxy)-3,5-difluoropyridin-2-yl)oxy]benzonitrile;

4-benzyloxy-3-[(4-(1-ethoxycarbonyl-4-guanidinobutoxy)-6-(3-(1-methylimidazolin-2-yl)phenoxy)-3,5-difluoropyridin-2-yl)oxy]benzonitrile; and 4-benzyloxy-3-[(4-(1-ethoxycarbonyl-4-guanidinobutoxy)-6-(3-(1-methylimidazol-2-yl)phenoxy)-3,5-difluoropyridin-2-yl)oxy]benzonitrile.

PREPARATION 6

Compounds of Formula (N)

A. To a solution of ethyl 2-hydroxy-4-methylvalerate (0.50 g, 2.5 mmol) in dry DMF (25 mL) was added pentafluoropyridine (0.31 mL, 0.47 g, 2.8 mmol) and cesium carbonate (1.1 g, 3.3 mmol). The resultant mixture was heated to 45° C. and stirred at that temperature for 10 days, then poured into 100 mL of water and 100 mL of ethyl acetate. The aqueous layer was separated and extracted with another 500 mL of ethyl acetate. The combined organic extracts were shed with water (100 mL) then brine (100 mL), dried over $MgSO_4$, filtered, and concentrated in vacuo to afford 0.87 g (99% yield) of 4-(1-ethoxycarbonyl-3-methylbutyl)oxy-2,3,5,6-tetrafluoropyridine as a clear, yellow liquid: NMR ($CDCl_3$) 5.2 (d, 1), 4.3–4.1 (m, 3), 2.0 (m, 1), 1.8 (m, 1), 1.3 (m, 3), 1.0 (m, 6) ppm.

B. In a similar manner, the following compounds are made:
4-(1-ethoxycarbonyl-3-methylbutyl)oxy-2,3,5,6-tetrafluoropyridine;
4-(1-ethoxycarbonyl-2-methylpropyl)oxy-2,3,5,6-tetrafluoropyridine;
4-(1-ethoxycarbonyl-2-methylbutyl)oxy-2,3,5,6-tetrafluoropyridine;
4-(1-ethoxycarbonyl-2-mercaptoethyl)oxy-2,3,5,6-tetrafluoropyridine;
4-(1-ethoxycarbonyl-3-methylthiopropyl)oxy-2,3,5,6-tetrafluoropyridine;
4-(1-ethoxycarbonyl-2-hydroxyethyl)oxy-2,3,5,6-tetrafluoropyridine;
4-(1-ethoxycarbonyl-2-hydroxypropyl)oxy-2,3,5,6-tetrafluoropyridine;
4-(1-ethoxycarbonyl-2-carboxyethyl)oxy-2,3,5,6-tetrafluoropyridine;
4-(1-ethoxycarbonyl-2-aminocarbonylethyl)oxy-2,3,5,6-tetrafluoropyridine;
4-(1-ethoxycarbonyl-3-carboxypropyl)oxy-2,3,5,6-tetrafluoropyridine;
4-(1-ethoxycarbonyl-3-aminocarbonylpropyl)oxy-2,3,5,6-tetrafluoropyridine;
4-(1-ethoxycarbonyl-2-imidazol-4-ylethyl)oxy-2,3,5,6-tetrafluoropyridine;
4-(1ethoxycarbonyl-2-phenylmethylethyl)oxy-2,3,5,6-tetrafluoropyridine;
4-(1-ethoxycarbonyl-2-indol-3-ylethyl)oxy-2,3,5,6-tetrafluoropyridine;
4-(1-ethoxycarbonyl-4-guanidinobutyl)oxy-2,3,5,6-tetrafluoropyridine; and
4-(1-ethoxycarbonyl-4-aminobutyl)oxy-2,3,5,6-tetrafluoropyridine.

PREPARATION 7

Compounds of Formula (Q)

A. To a solution of 4-benzyloxy-3-[(4-(N-(1-tert-butoxycarbonyl-5-(N-tert-butoxycarbonylamino)pentyl)amino)-6-(3-(1-methyl)imidazol-2-yl)phenoxy-3,5-difluoropyridin-2-yl)oxy]benzonitrile (600 mg, 0.74 mmol) in 25 mL of $CH_2Cl_2$ was added 25 mL of TFA. The resulting mixture was stirred at ambient temperature for 1.5 hours, then all volatiles removed in vacuo. The residue was dissolved in 25 mL of a 3:2 mixture of methanol/water and $K_2CO_3$ was added until pH 11 was reached (1.05 g, 7.4 mmol), followed by amidinyl sulfonic acid (275 mg, 2.22 mmol). After 30 minutes, an aliquot was withdrawn and analyzed by HPLC on a C18 Dynamax column with 20–80% acetonitrile in water gradient with 0.1% trifluoroacetic acid to show complete reaction had occurred. The reaction mixture was concentrated in vacuo to remove the solvent and the resulting aqueous solution extracted thrice with acetonitrile. The combined organic extracts were washed with brine, filtered through a column of celite and concentrated to 800 mg of 4-benzyloxy-3-[(4-(N-(carboxy-5-guanidinopentyl)amino)-6-(3-(1-methyl) imidazol-2-yl) phenoxy-3,5-difluoropyridin-2-yl)-oxy]benzonitrile as an oil.

B. In a similar manner, the following compound was made:
4-benzyloxy-3-[(4-(N-(carboxy-5-guanidinylpentyl)amino)-6-(3-(1-methyl)imidazolin-2-yl)phenoxy-3,5-difluoropyridin-2-yl)oxy]benzonitrile.

C. In a similar manner, the following compound is made:
4-benzyloxy-3-[(4-(N-methyl-N-(carboxy-5-guanidinopentyl)amino)-6-(3-(1-methyl)imidazolin-2-yl)phenoxy-3,5-difluoropyridin-2-yl)oxy]benzonitrile.

EXAMPLE 1

Compounds of Formula (Ia)

A. A solution of 4-benzyloxy-3-[(4-(N-methyl-N-(1-ethoxycarbonyl-1-methylethyl)amino)-6-(3-(1-methyl)imidazolin-2-yl)phenoxy-3,5difluoropyridin-2-yl)-oxy]benzonitrile (0.98 g, 1.46 mmol) in absolute ethanol (40 mL) was cooled to −78° C. and HCl(g) was bubbled through the mixture for 15 minutes. The resultant mixture was stirred at ambient temperature for 20 hours, then concentrated in vacuo without heating to afford a white foam. This foam was dissolved in absolute ethanol (40 mL) and heated to reflux as $NH_3$(g) was gently bubbled through the mixture. After 2 hours the mixture was cooled to ambient temperature and concentrated in vacuo. Purification by HPLC on a C18 Dynamax column with 20–80% acetonitrile in water gradient with 0.1% trifluoroacetic acid afforded 4-hydroxy-3-[(4-(N-methyl-N-(1-ethoxycarbonyl-1-methylethyl)amino)-6-(3-(1-methylimidazolin-2-yl)phenoxy)-3,5-difluoropyridin-2-yl)oxy]benzamidine, trifluoroacetic acid salt as a white solid: NMR (DMSO-$d_6$) 10.2 (br s, 1), 9.0 (br s , 2), 8.7 (br s, 2), 7.3–7.6 (m, 6), 7.0 (d, 2), 3.94.2 (m, 6), 3.0 (s, 3), 2.9 (s, 3), 1.5 (s, 3), 1.1 (t, 3) ppm.

B. In a similar manner, other compounds of the invention were made:
4-hydroxy-3-[(4-(N-(1-carboxy-5-guanidinopentyl)amino)-6-(3-(1-methylimidazolin-2-yl)phenoxy)-3,5-difluoropyridin-2-yl)oxy]benzamidine; NMR (DMSO-d6) 11.1 (br s, 1), 10.3 (br s, 1), 9.1 (br s, 2), 8.9 (br s, 2), 7.0–7.7 (m, 10), 6.6 (d, 1), 4.3 (m, 1), 4.0 (m, 2), 3.9 (m, 2), 3.1 (m, 2), 3.0 (s, 3), 1.8 (m, 2), 1.5 (m, 4)
4-hydroxy-3-[(4-(1-ethoxycarbonyl-3-methylbutoxy)-6-(3-(1-methylimidazolin-2-yl)phenoxy)-3,5-difluoropyridin-2-yl)oxy]benzamidine; NMR (DMSO-$d_6$ 10.2 (s, 1), 9.0 (br s, 2), 8.8 (br s, 2), 7.3-7.6 (m, 6), 7.0 (d, 1), 5.2 (m, 1), 4.2 (q, 2), 3.9–4.1 (m, 4), 2.9 (s, 3), 1.7–2.0 (m, 3), 1.2 (t, 3), 1.0 (s, 3), 0.95 (s, 3) ppm; and
4-hydroxy-3-[(4-(N-methyl-N-(1-ethoxycarbonylethyl)amino)-6-(3-(1-methylimidazolin-2-yl)phenoxy)-3,5-difluoropyridin-2-yl)oxy]benzamidine; NMR (DMSO-$d_6$) 10.2 (br s, 1), 9.0 (br s , 2), 8.8 (br s, 2), 7.3–7.6 (m, 6), 7.0 (d, 2), 4.4 (q, 2), 3.8–4.2 (m, 5), 3.0 (s, 3), 2.9 (s, 3), 1.4 (d, 3), 1.2 (t, 3) ppm.

C. In a similar manner, the following compounds are made:

4-hydroxy-3-[(4-(N-ethyl-N-(1-ethoxycarbonyl-1-methylethyl)amino)-6-(3-(1-methylimidazolin-2-yl)phenoxy)-3,5-difluoropyridin-2-yl)oxy]benzamidine;

4-hydroxy-3-[(4-(N-propyl-N-(1-ethoxycarbonyl-1-methylethyl)amino)-6-(3-(1-methylimidazolin-2-yl)phenoxy)-3,5-difluoropyridin-2-yl)oxy]benzamidine;

4-hydroxy-3-[(4-(N-butyl-N-(1-ethoxycarbonyl-1-methylethyl)amino)-6-(3-(1-methylimidazolin-2-yl)phenoxy)-3,5-difluoropyridin-2-yl)oxy]benzamidine;

4-hydroxy-3-[(4-(N-phenyl-N-(1-ethoxycarbonyl-1-methylethyl)amino)-6-(3-(1-methylimidazolin-2-yl)phenoxy)-3,5-difluoropyridin-2-yl)oxy]benzamidine;

4-hydroxy-3-[(4-(N-benzyl-N-(1-ethoxycarbonyl-1-methylethyl)amino)-6-(3-(1-methylimidazolin-2-yl)phenoxy)-3,5-difluoropyridin-2-yl)oxy]benzamidine;

4-hydroxy-3-[(4-(N-(3-ethoxycarbonylpropyl)-N-(1-ethoxycarbonyl-1-methylethyl)amino)-6-(3-(1-methylimidazolin-2-yl)phenoxy)-3,5difluoropyridin-2-yl)oxy] benzamidine;

4-hydroxy-3-[(4-(N-(4-aminocarbonylbutyl)-N-(1-ethoxycarbonyl-1-methylethyl)amino)-6-(3-(1-methylimidazolin-2-yl)phenoxy)-3,5-difluoropyridin-2-yl)oxy]benzamidine;

4-hydroxy-3-[(4-(N-(4-aminobutyl)-N-(1-ethoxycarbonyl-1-methylethyl)amino)-6-(3-(1-methylimidazolin-2-yl)phenoxy)-3,5-difluoropyridin-2-yl)oxy]benzamidine;

4-hydroxy-3-[(4-(N-propyl-N-(1-ethoxycarbonyl-3-methylbutyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-methylpropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-methylbutyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-mercaptoethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-3-methylthiopropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-hydroxyethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-hydroxypropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-carboxyethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-carboxyethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-aminocarbonylethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-3-carboxylpropyl)amnino)-6-(3-(1-methylimidazolin-2-yl)phenoxy)-3,5-difluoropyridin-2-yl)oxy]benzamidine;

4-hydroxy-3-[(4-methyl-N-(1-ethoxycarbonyl-3-aminocarbonylpropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-imidazol-4-ylethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-phenylmethylethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-2-indol-3-ylethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-4-guanidinobutyl)amino)-6-(3-(1-methylimidazolin-2-yl)phenoxy)-3,5-difluoropyridin-2-yl)oxy]benzamidine;

4-hydroxy-3-[(4-(N-methyl-N-(1-ethoxycarbonyl-4-guanidinobutyl)amino)-6-(3-(1-methylimidazolin-2-yl)phenoxy)-3,5-difluoropyridin-2-yl)oxy]benzamidine;

4-hydroxy-3-[(4-(1-ethoxycarbonyl-1-methylethoxy)-6-(3-(1-methylimidazol-2-yl)phenoxy)-3,5-difluoropyridin-2-yl)oxy]benzamidine;

4-hydroxy-3-[(4-(1-ethoxycarbonyl -1-methylethoxy)-6-(3-(1-methylimidazol-2-yl)phenoxy)-3,5-difluoropyridin-2-yl)oxy]benzamidine;

4-hydroxy-3-[(4-(1-ethoxycarbonyl-1-methylethoxy)-6-(3-(1-methylimidazolin-2-yl)phenoxy)-3,5-difluoropyridin-2-yl)oxy]benzamidine;

4-hydroxy-3-[(4-(1-ethoxycarbonyl-1-methylethoxy)-6-(3-(1-methylimidazol-2-yl)phenoxy)-3,5-difluoropyridin-2-yl)oxy]benzamidine;

4-hydroxy-3-[(4-(1-ethoxycarbonyl-1-methylethoxy)-6-(3-(1-methyl imidazol-2-yl)phenoxy)-3,5-difluoropyridin-2-yl)oxy]benzamidine;

4-hydroxy-3-[(4-(1-ethoxycarbonyl-1-methylethoxy)-6-(3-(1-methylimidazolin-2-yl)phenoxy)-3,5-difluoropyridin-2-yl)oxy]benzamidine;

4-hydroxy-3-[(4-(1-ethoxycarbonyl-1-methylethoxy)-6-(3-(1-methylimidazolin-2-yl)phenoxy)-3,5-difluoropyridin-2-yl)oxy]benzamidine;

4-hydroxy-3-[(4-(1-ethoxycarbonyl-1-methylethoxy)-6-(3-(1-methylimidazol-2-yl)phenoxy)-3,5-difluoropyridin-2-yl)oxy]benzamidine;

4-hydroxy-3-[(4-(1-ethoxycarbonyl-3-methylbutoxy)-6-(3-(1-methylimidazol-2-yl)phenoxy)-3,5-difluoropyridin-2-yl)oxy]benzamidine;

4-hydroxy-3-[(4-(1-ethoxycarbonyl-2-methylpropoxy)-6-(3-(1-methylimidazolin-2-yl)phenoxy)-3,5-difluoropyridin-2-yl)oxy]benzamidine;

4-hydroxy-3-[(4-(1-ethoxycarbonyl-2-methylbutoxy)-6-(3-(1-methylimidazolin-2-yl)phenoxy)-3,5-difluoropyridin-2-yl)oxy]benzamidine;

4-hydroxy-3-[(4-(1-ethoxycarbonyl-2-mercaptoethoxy)-6-(3-(1-methylimidazolin-2-yl)phenoxy)-3,5-difluoropyridin-2-yl)oxy]benzamidine;

4-hydroxy-3-[(4-(1-ethoxycarbonyl-3-methylthiopropoxy)-6-(3-(1-methylimidazolin-2-yl)phenoxy)-3,5-difluoropyridin-2-yl)oxy]benzamidine;

4-hydroxy-3-[(4-(1-ethoxycarbonyl-2-hydroxyethoxy)-6-(3-(1-methylimidazol-2-yl)phenoxy)-3,5-difluoropyridin-2-yl)oxy]benzamidine;

4-hydroxy-3-[(4-(1-ethoxycarbonyl-2-hydroxypropoxy)-6-(3-(1-methylimidazolin-2-yl)phenoxy)-3,5-difluoropyridin-2-yl)oxy]benzamidine;

4-hydroxy-3-[(4-(1-ethoxycarbonyl-2-carboxyethoxy)-6-(3-(1-methylimidazol-2-yl)phenoxy)-3,5-difluoropyridin-2-yl)oxy]benzamidine;

4-hydroxy-3-[(4-(1-ethoxycarbonyl-2-carboxyethoxy)-6-(3-(1-methylimidazolin-2-yl)phenoxy)-3,5-difluoropyridin-2-yl)oxy]benzamidine;

4-hydroxy-3-[(4-(1-ethoxycarbonyl-2-aminocarbonylethoxy)-6-(3-(1-methylimidazol-2-yl)phenoxy)-3,5-difluoropyridin-2-yl)oxy]benzamidine;

4-hydroxy-3-[(4-(1-ethoxycarbonyl-3-carboxylpropoxy)-6-(3-(1-methylimidazolin-2-yl)phenoxy)-3,5-difluoropyridin-2-yl)oxy]benzamidine;

4-hydroxy-3-[(4-(1-ethoxycarbonyl-3-aminocarbonylpropoxy)-6-(3-(1-methylimidazolin-2-yl)phenoxy)-3,5-difluoropyridin-2-yl)oxy]benzamidine;

4-hydroxy-3-[(4-(1-ethoxycarbonyl-2-imidazol-4-ylethoxy)-6-(3-(1-methylimidazolin-2-yl)phenoxy)-3,5-difluoropyridin-2-yl)oxy]benzamidine;

4-hydroxy-3-[(4-(1-ethoxycarbonyl-2-phenylmethylethoxy)-6-(3-(1-methylimidazol-2-yl)phenoxy)-3,5-difluoropyridin-2-yl)oxy]benzamidine;

4-hydroxy-3-[(4-(1-ethoxycarbonyl-2-indol-3-ylethoxy)-6-(3-(1-methylimidazol-2-yl)phenoxy)-3,5-difluoropyridin-2-yl)oxy]benzamidine;

4-hydroxy-3-[(4-(1-ethoxycarbonyl-4-guanidinobutoxy)-6-(3-(1-methylimidazolin-2-yl)phenoxy)-3,5-difluoropyridin-2-yl)oxy]benzamidine; and 4-hydroxy-3-[(4-(1-ethoxycarbonyl-4-guanidinobutoxy)-6-(3-(1-methylimidazol-2-yl)phenoxy)-3,5-difluoropyridin-2-yl)oxy]benzamidine.

EXAMPLE 2

Compounds of Formula (Ib)

A. A solution of 4-hydroxy-3-[(4-(N-methyl-N-(1-ethoxycarbonyl-1-methylethyl)amino)-6-(3-(1-methyl)imidazolin-2-yl)phenoxy-3,5-difluoropyridin-2-yl)oxy]benzamidine, trifluoroacetic acid salt (0.10 g, 0.11 mmol) in 12 mL of 6 N aqueous HCl was stirred at 65° C. for 1 hour. It was then cooled to ambient temperature, diluted with acetonitrile and trifluoroacetic acid and purified by HPLC on a C18 Dynamax column with 20–80% acetonitrile in water gradient with 0.1% trifluoroacetic acid to afford 4-hydroxy-3-[(4-(N-methyl-N-(carboxy-1-methylethyl)amino)-6-(3-(1-methylimidazolin-2-yl)phenoxy)-3,5-difluoropyridin-2-yl)oxy]benzamidine, trifluoroacetic acid salt, as a white solid: NMR (DMSO-$d_6$)/TFA) 10.2 (br s, 1), 9.0 (br s , 2), 8.8 (br s, 2), 7.3–7.6 (m, 6), 7.0 (d, 2), 4.1 (m, 2), 3.9 (m, 2), 3.0 (s, 3), 2.9 (s, 3), 1.4 (s, 3) ppm.

B. In a similar manner, the following compounds were made:

4-hydroxy-3-[(4-(1-carboxy-3-methylbutoxy)-6-(3-(1-methylimidazolin-2-yl)phenoxy)-3,5-difluoropyridin-2-yl)oxy]benzamidine; NMR (DMSO-$d_6$) 9.0 (br s, 2), 8.8 (br s, 2), 7.3–7.6 (m, 6), 7.0 (d, 1), 5.2 (m, 1), 3.94.1.(m, 4), 2.9 (s, 3), 1.7–2.0 (m, 3), 1.0 (s, 3), 0.95 (s, 3) ppm;

4-hydroxy-3-[(4-(N-methyl-N-(1-carboxyethyl)amino)-6-(3-(1-methylimidazolin-2-yl)phenoxy)-3,5-difluoropyridin-2-yl)oxy]benzamidine; NMR (DMSO-$d_6$) 10.2 (br s, 1), 9.0 (br s , 2), 8.8 (br s, 2), 7.3–7.6 (m, 6), 7.0 (d, 2), 4.3 (q, 2), 4.1 (m, 2), 3.9 (m, 2), 3.0 (s, 3), 2.9 (s, 3), 1.4 (d, 3) ppm;

C. In a similar manner, the following compounds are made:

4-hydroxy-3-[(4-(N-ethyl-N-(1-carboxy-1-methylethyl)amino)-6-(3-(1 -methylimidazolin-2-yl)phenoxy)-3,5-difluoropyridin-2-yl)oxy]benzamidine;

4-hydroxy-3-[(4-(N-propyl-N-(1-carboxy-1-methylethyl)amino)-6-(3-(1-methylimidazolin-2-yl)phenoxy)-3,5-difluoropyridin-2-yl)oxy]benzamidine;

4-hydroxy-3-[(4-(N-butyl-N-(1-carboxy-1-methylethyl)amino)-6-(3-(1-methylimidazolin-2-yl)phenoxy)-3,5-difluoropyridin-2-yl)oxy]benzamidine;

4-hydroxy-3-[(4-(N-phenyl-N-(1-carboxy-1-methylethyl)amino)-6-(3-(1-methylimidazolin-2-yl)phenoxy)-3,5-difluoropyridin-2-yl)oxy]benzamidine;

4-hydroxy-3-[(4-(N-benzyl-N-(1-carboxy-1-methylethyl)amino)-6-(3-(1-methylimidazolin-2-yl)phenoxy)-3,5difluoropyridin-2-yl)oxy]benzamidine;

4-hydroxy-3-[(4-(N-(3-carboxypropyl)-N-(1-carboxy-1-methylethyl)amino)-6-(3-(1-methylimidazolin-2-yl)phenoxy)-3,5-difluoropyridin-2-yl)oxy]benzamidine;

4-hydroxy-3-[(4-(N-(4-aminocarbonylbutyl)-N-(1-carboxy-1-methylethyl)amino)-6-(3-(1-methylimidazolin-2-yl)phenoxy)-3,5-difluoropyridin-2-yl)oxy]benzamidine;

4-hydroxy-3-[(4-(N-(4-aminobutyl)-N-(1-carboxy-1-methylethyl)amino)-6-(3-(1-methylimidazolin-2-yl)phenoxy)-3,5-difluoropyridin-2-yl)oxy]benzamidine;

4-hydroxy-3-[(4-(N-propyl-N-(1-carboxy-3-methylbutyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-methylpropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-methylbutyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-mercaptoethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-3-methylthiopropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-hydroxyethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-hydroxypropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-carboxyethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-carboxyethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-aminocarbonylethyl)amino)-6-(3-(1 -methylimidazolin-2-yl)phenoxy)-3,5-difluoropyridin-2-yl)oxy]benzamidine;

4-hydroxy-3-[(4-(N-methyl-N-(1-carboxy-3-carboxylpropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-3-aminocarbonylpropyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-imidazol-4-ylethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-phenylmethylethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-2-indol-3-ylethyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-4-guanidinobutyl)amino)-6-(3-(1-methylimidazolin-2-yl)phenoxy)-3,5-difluoropyridin-2-yl)oxy]benzamidine;

4-hydroxy-3-[(4-(N-methyl-N-(1-carboxy-4-guanidinobutyl)amino)-6-(3-(1-methylimidazolin-2-yl)phenoxy)-3,5-difluoropyridin-2-yl)oxy]benzamidine;

4-hydroxy-3-[(4-(1-carboxy-1-methylethoxy)-6-(3-(1-methylimidazol-2-yl)phenoxy)-3,5-difluoropyridin-2-yl)oxy]benzamidine;

4-hydroxy-3-[(4-(1-carboxy-1-methylethoxy)-6-(3-(1-methylimidazol-2-yl)phenoxy)-3,5-difluoropyridin-2-yl)oxy]benzamidine;

4-hydroxy-3-[(4-(1-carboxy-1-methylethoxy)-6-(3-(1-methylimidazol-2-yl)phenoxy)-3,5difluoropyridin-2-yl)oxy]benzamidine;

4-hydroxy-3-[(4-(1-carboxy-1-methylethoxy)-6-(3-(1-methylimidazol-2-yl)phenoxy)-3,5-difluoropyridin-2-yl)oxy]benzamidine;

4-hydroxy-3-[(4-(1-carboxy-1-methylethoxy)-6-(3-(1-methylimidazol-2-yl)phenoxy)-3,5-difluoropyridin-2-yl)oxy]benzamidine;

4-hydroxy-3-[(4-(1-carboxy-1-methylethoxy)-6-(3-(1-methylimidazolin-2-yl)phenoxy)-3,5-difluoropyridin-2-yl)oxy]benzamidine;

4-hydroxy-3-[(4-(1-carboxy-1-methylethoxy)-6-(3-(1-methylimidazolin-2-yl)phenoxy)-3,5-difluoropyridin-2-yl)oxy]benzamidine;

4-hydroxy-3-[(4-(1-carboxy-1-methylethoxy)-6-(3-(1-methylimidazol-2-yl)phenoxy)-3,5-difluoropyridin-2-yl)oxy]benzamidine;

4-hydroxy-3-[(4-(1-carboxy-3-methylbutoxy)-6-(3-(1-methylimidazol-2-yl)phenoxy)-3,5-difluoropyridin-2-yl)oxy]benzamidine;

4-hydroxy-3-[(4-(1-carboxy-2-methylpropoxy)-6-(3-(1-methylimidazolin-2-yl)phenoxy)-3,5-difluoropyridin-2-yl)oxy]benzamidine;

4-hydroxy-3-[(4-(1-carboxy-2-methylbutoxy)-6-(3-(1-methylimidazolin-2-yl)phenoxy)-3,5-difluoropyridin-2-yl)oxy]benzamidine;

4-hydroxy-3-[(4-(1-carboxy-2-mercaptoethoxy)-6-(3-(1-methylimidazolin-2-yl)plienoxy)-3,5-difluoropyridin-2-yl)oxy]benzamidine;

4-hydroxy-3-[(4-(1-carboxy-3-methylthiopropoxy)-6-(3-(1-methylimidazol-2-yl)phenoxy)-3,5-difluoropyridin-2-yl)oxy]benzamidine;

4-hydroxy-3-[(4-(1-carboxy-2-hydroxyethoxy)-6-(3-(1-methylimidazol-2-yl)phenoxy)-3,5-difluoropyridin-2-yl)oxy]benzamidine;

4-hydroxy-3-[(4-(1-carboxy-2-hydroxypropoxy)-6-(3-(1-methylimidazolin-2-yl)phenoxy)-3,5-difluoropyridin-2-yl)oxy]benzamidine;

4-hydroxy-3-[(4-(1-carboxy-2-carboxyethoxy)-6-(3-(1-methylimidazol-2-yl)phenoxy)-3,5-difluoropyridin-2-yl)oxy]benzamidine;

4-hydroxy-3-[(4-(1-carboxy-2-carboxyethoxy)-6-(3-(1-methylimidazol-2-yl)phenoxy)-3,5-difluoropyridin-2-yl)oxy]benzamidine;

4-hydroxy-3-[(4-(1-carboxy-2-aminocarbonylethoxy)-6-(3-(1-methylimidazol-2-yl)phenoxy)-3,5-difluoropyridin-2-yl)oxy]benzamidine;

4-hydroxy-3-[(4-(1-carboxy-3-carboxylpropoxy)-6-(3-(1-methylimidazolin-2-yl)phenoxy)-3,5-difluoropyridin-2-yl)oxy]benzamidine;

4-hydroxy-3-[(4-(1-carboxy-3-aminocarbonylpropoxy)-6-(3-(1-methylimidazolin-2-yl)phenoxy)-3,5-difluoropyridin-2-yl)oxy]benzamidine;

4-hydroxy-3-[(4-(1-carboxy-2-imidazol-4-ylethoxy)-6-(3-(1-methylimidazolin-2-yl)phenoxy)-3,5-difluoropyridin-2-yl)oxy]benzamidine;

4-hydroxy-3-[(4-(1-carboxy-2-phenylmethylethoxy)-6-(3-(1-methylimidazol-2-yl)phenoxy)-3,5-difluoropyridin-2-yl)oxy]benzamidine;

4-hydroxy-3-[(4-(1-carboxy-2-indol-3-ylethoxy)-6-(3-(1-methylimidazol-2-yl)phenoxy)-3,5-difluoropyridin-2-yl)oxy]benzamidine;

4-hydroxy-3-[(4-(1-carboxy-4-guanidinobutoxy)-6-(3-(1-methylimidazolin-2-yl)phenoxy)-3,5-difluoropyridin-2-yl)oxy]benzamidine; and 4-hydroxy-3-[(4-(1-carboxy-4-guanidinobutoxy)-6-(3-(1-methylimidazol-2-yl)phenoxy)-3,5-difluoropyridin-2-yl)oxy]benzamidine.

EXAMPLE 3

Compounds of Formula (Ic)

A. A solution of 4-benzyloxy-3-[(4-(N-(1-tert-butoxycarbonyl-5-(N-(tert-butoxycarbonyl)amino)pentyl)amino)-6-(3-(1-methyl)imidazol-2-yl)phenoxy-3,5-difluoropyridin-2-yl)oxy]benzonitrile (890 mg, 1.1 mmol) in 15 mL of a 1:1 mixture of ethanol/methylene chloride was cooled to −10° C. and HCl(g) was bubbled through the mixture for 15 minutes. The resultant mixture was stirred at ambient temperature for 20 hours, then concentrated off all volatiles in vacuo without heating to afford a solid white foam. This foam was dissolved in absolute ethanol (40 mL) and cooled to −10° C. as $NH_3$(g) was gently bubbled through the mixture for 15 minutes. The mixture was then heated to 65° C. for 2 hours, then cooled to ambient temperature and concentrated in vacuo. The resulting residue was dissolved in 10 mL of 6 N aqueous HCl and heated to 85° C. for 4 hours. The mixture was cooled to ambient temperature and purified by preparative-HPLC on a C18 Dynamax column with 20–80% acetonitrile in water gradient with 0.1% trifluoroacetic acid to afford 4-hydroxy-3-[(4-(N-(1-carboxy-5-aminopentyl)amino)-6-(3-(1-methyl)imidazol-2-yl)phenoxy-3,5-difluoropyridin-2-yl)oxy]benzamidine; NMR (DMSO-$d_6$) 8.9 (br s, 2), 8.6 (br s, 2), 7.7–7.2 (m, 12), 6.8–7.7 (m, 9), 6.5 (br s, 1), 4.4 (m, 1), 3.7 (s, 3), 2.8 (m, 2), 1.9 (m, 2), 1.5 (m, 4) ppm.

B. In a similar manner, the following compound was made:

4-hydroxy-3-[(4-(N-(1-carboxy-5-guanidinopentyl)amino)-6-(3-(1-methyl)imidazol-2-yl)phenoxy-3,5-difluoropyridin-2-yl)oxy]benzamidine; NMR (DMSO-$d_6$) 8.9 (br s, 2), 8.6 (br s, 2), 6.3–7.7 (m, 17), 4.4 (m, 1), 3.7 (s, 3), 3.1 (m, 2), 1.9 (m, 2), 1.5 (m, 4) ppm;

C. In a similar manner, the following compound is made:
4-hydroxy-3-[(4-(N-(1-carboxy-5-aminopentyl)amino)-6-(3-(1-methyl)imidazolin-2-yl)phenoxy-3,5-difluoropyridin-2-yl)oxy]benzamidine.

EXAMPLE 4

Compounds of Formula (Id)

A. To a solution of 4-hydroxy-3-[(4-(N-(1-carboxy-5-aminopentyl)amino)-6-(3-(1-methyl)imidazol-2-yl)phenoxy-3,5-difluoropyridin-2-yl)oxy]benzamidine (271 mg, 0.47 mmol) in 12 mL of a 4:1 mixture of methanol/water was added $K_2CO_3$ (193 mg, 1.4 mmol, pH 8–9) and ethyl acetimidate hydrochloride (172 mg, 1.4 mmol). After stirring for 1 hour, the mixture was filtered and purified by preparative HPLC on a C18 Dynamax column with 20–80% acetonitrile in water gradient with 0.1% trifluoroacetic acid to afford 4-hydroxy-3-[(4-(N-(1-carboxy-5-(N-(1-iminoethyl)amino)pentyl)amino)-6-(3-(1-methyl)imidazol-2-yl)phenoxy-3,5-difluoropyridin-2-yl)oxy]benzamidine; NMR (DMSO-$d_6$) 9.3 (br s, 1), 8.9 (br s, 3), 8.6 (br s, 2), 8.4 (br s, 2), 7.4–7.7 (m, 9), 7.2 (d, 1), 6.8 (d, 1), 4.4 (m, 1), 3.7 (s, 3), 3.2 (m, 2), 2.1 (s, 3), 1.9 (m, 2), 1.5 (m, 4) ppm.

B. In a similar manner, the following compound was made:
4-hydroxy-3-[(4-(N-(1-carboxy-5-(N-(1-iminoethyl)amino)pentyl)amino)-6-(3-(1-methyl)imidazolin-2-yl)phenoxy-3,5-difluoropyridin-2-yl)oxy]benzamidine; NMR (DMSO-$d_6$) 10.3 (br s, 1), 9.4 (br s , 1), 9.0 (br s, 3), 8.7 (br s, 2), 8.5 (br s, 1), 7.0–7.7 (m, 7), 6.3 (br s., 1), 4.4 (m, 1), 4.1 (m, 2), 3.9 (m, 2), 3.3 (m, 2), 3.0 (s, 3), 2.2 (s, 3), 1.8 (m, 2), 1.5 (m, 4) ppm.

EXAMPLE 5

This example illustrates the preparation of representative pharmaceutical compositions for oral administration containing a compound of the invention, or a pharmaceutically acceptable salt thereof, e.g., 4-hydroxy-3-[(4-(N-methyl-N-(1-carboxy-1-methylethyl)amino)-6-(3-(1-methyl)imidazolin-2-yl)phenoxy-3,5-difluoropyridin-2-yl)oxy]benzamidine:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 79.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 6

This example illustrates the preparation of a representative pharmaceutical formulation for parenteral administration containing a compound of the invention, or a pharmaceutically acceptable salt thereof, e.g., 4-hydroxy-3-[(4-(N-methyl-N-(1-ethoxycarbonyl-1-methylethyl)amino)-6-(3-(1-methyl)imidazolin-2-yl)phenoxy-3,5-difluoropyridin-2-yl)oxy]benzamidine:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 $\mu$ membrane filter and packaged under sterile conditions.

EXAMPLE 7

This example illustrates the preparation of a representative pharmaceutical composition in suppository form containing a compound of the invention, or a pharmaceutically acceptable salt thereof, e.g., 4-hydroxy-3-[(4-(N-methyl-N-(1-ethoxycarbonylethyl)amino)-6-(3-(1-methyl)imidazolin-2-yl)phenoxy-3,5Sdifluoropyridin-2-yl)oxy]benzamidine:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 8

This example illustrates the preparation of a representative pharmaceutical formulation for insufflation containing a compound of the invention, or a -pharmaceutically acceptable salt thereof, e.g., 4-hydroxy-3-[(4-(N-methyl-N-(1-carboxy-1-methylethyl)amino)-6-(3-(1-methyl)imidazolin-2-yl)phenoxy-3,5-difluoropyridin-2-yl)oxy]benzamidine:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 9

This example illustrates the preparation of a representative pharmaceutical formulation in nebulized form containing a compound of the invention, or a pharmaceutically acceptable salt thereof, e.g., 4-hydroxy-3-[(4-(N-(1-carboxy-5-aminopentyl)amino)- 6-(3-(1-methyl)imidazolin-2-yl)phenoxy-3,5-difluoropyridin-2-yl)oxy]-benzamidine:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 10

This example illustrates the preparation of a representative pharmaceutical formulation in aerosol form containing a compound of the invention, or a pharmaceutically acceptable salt thereof, e.g., 4-hydroxy-3-[(4-(N-(1-carboxy-5-guanidinopentyl)amino)-6-(3-(1-methyl)imidazol-2-yl)phenoxy-3,5-difluoropyridin-2-yl)oxy]benzamidine:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 11

(In vitro assay for Factor Xa and Thrombin)

This assay demonstrates the activity of the compounds of the invention towards factor Xa, thrombin and tissue plasminogen activator. The activities were determined as an initial rate of cleavage of the peptide p-nitroanilide by the enzyme. The cleavage product, p-nitroaniline, absorbs at 405 nm with a molar extinction coefficient of 9920 $M^{-1}cm^{-1}$.

Reagents and Solutions:
Dimethyl sulfoxide (DMSO) (Baker analyzed grade).
Assay buffer:
  50 mM TrisHCl, 150 mM NaCl, 2.5 mM $CaCl_2$, and 0.1% polyethylene glycol 6000, pH 7.5.

Enzymes (Enzyme Research Lab.):
1. Human factor Xa stock solution: 0.281 mg/mL in assay buffer, stored at −80° C. (working solution (2X): 106 ng/mL or 2 nM in assay buffer, prepare prior to use).
2. Human thrombin stock solution: Stored at −80° C. (working solution (2X): 1200 ng/mL or 40 nM in assay buffer, prepare prior to use).
3. Human tissue plasminogen activator (tPA) (Two chains, Sigma) stock solution: 1 mg/mL, stored at −80° C. (working solution (2X): 1361 ng/mL in assay buffer, prepare prior to use).

Chromogenic substrates (Pharmacia Hepar Inc.):
1. S2222 (FXa assay) stock solution: 6 mM in $dH_2O$, store at 4° C. (working solution (4X): 656 AM in assay buffer).
2. S2302 (Thrombin assay) stock solution: 10 mM in $dH_2O$, stored at 4° C. (working solution (4X): 1200 AM in assay buffer).
3. S2288 (tPA assay) stock solution: 10 mM in $dH_2O$, stored at 4° C. (working solution (4X): 1484 AM in assay buffer).

(All substrate working solutions were prepared on assay day 5.)

Standard inhibitor compound stock solution:
  5 mM in DMSO, stored at −20° C.
Test compounds (compounds of the invention) stock solutions:
  10 mM in DMSO, stored at −20° C.

Assay procedure:
Assays were performed in 96-well microtiter plates in a total volume of 200 μl. Assay components were in final concentration of 50 mM TrisHCl, 150 mM NaCl, 2.5 mM $CaCl_2$, 0.1% polyethylene glycol 6000, pH 7.5, in the absence or presence of the standard inhibitor or the test compounds and enzyme and substrate at following concentrations: (1) 1 nM factor Xa and 164 μM S2222; (2) 20 nM thrombin and 300 μM S2302; and (3) 10 nM tPA and 371 μM S2288. Concentrations of the standard inhibitor compound in the assay were from 5 μM to 0.021 μM in 1 to 3 dilution. Concentration of the test compounds in the assay typically were from 10 μM to 0.041 μM in 1 to 3 dilution. For potent test compounds, the concentrations used in the factor Xa assay were further diluted 100 fold (100 nM to 0.41 nM) or 1000 fold (10 nM to 0.041 nM). All substrate concentrations used are equal to their $K_m$ values under the present assay conditions. Assays were performed at ambient temperature.

The first step in the assay was the preparation of 10 mM test compound stock solutions in DMSO (for potent test compounds, 10 mM stock solutions were further diluted to 0.1 or 0.01 mM for the factor Xa assay), followed by the preparation of test compound working solutions (4X) by a serial dilutions of 10 mM stock solutions with Biomek 1000 (or Multiprobe 204) in 96 deep well plates as follows:

(a) Prepare a 40 μM working solution by diluting the 10 mM stock 1 to 250 in assay buffer in 2 steps: 1 to 100, and 1 to 2.5.

(b) Make another five serial dilutions (1:3) of the 40 μM solution (600 μl for each concentration). A total of six diluted test compound solutions were used in the assay. Standard inhibitor compound (5 mM stock) or DMSO (control) went through the same dilution steps as those described above for test compounds.

The next step in the assay was to dispense 50 μl of the test compound working solutions (4X) (from 40 uM to 0.164 uM) in duplicate to microtiter plates with Biomek or MP204. To this was added 100 μl of enzyme working solution (2X) with Biomek or MP204. The resulting solutions were incubated at ambient temperature for 10 minutes.

To the solutions was added 50 µl of substrate working solution (4X) with Biomek or MP204.

The enzyme kinetics were measured at 405 nm at 10 seconds intervals for five minutes in a THERMOmax plate reader at ambient temperature.

Calculation of $K_i$ of the BX compounds:

Enzyme rates were calculated as mOD/min based on the first two minutes readings. The $IC_{50}$ values were determined by fitting the data to the log-logit equation (linear) or the Morrison equation (non-linear) with an EXCEL spreadsheet. Ki values were then obtained by dividing the $IC_{50}$ by 2. Routinely, Ki(factor Xa) values than 3 nM were calculated from the Morrison equation.

Compounds of the invention, when tested in this assay, demonstrated the selective ability to inhibit human factor Xa and human thrombin.

EXAMPLE 12

(In vitro assay for Human Prothrombinase)

This assay demonstrates the ability of the compounds of the invention to inhibit prothrombinase. Prothrombinase (PTase) catalyzes the activation of prothrombin to yield fragment 1.2 plus thrombin with meizothrombin as the intermediate. This assay is an end point assay. Activity of the prothrombinase is measured by activity of thrombin (one of the reaction products) or by the amount of thrombin formed/time based on a thrombin standard curve (nM vs mOD/min). For determination of $IC_{50}$ (PTase) of the compounds of the invention, PTase activity was expressed by thrombin activity (mOD/min).

Materials:
Enzymes:
1. Human factor Va (Haematologic Technologies Inc., Cat# HCVA-0110) working solution: 1.0 mg/mL in 50% glycerol, 2 mM $CaCl_2$, stored at $-20°$ C.
2. Human factor Xa (Enzyme Res. Lab. cat# HFXa1011) working solution: 0.281 mg/mL in assay buffer (without BSA), stored at $-80°$ C.
3. Human prothrombin (FII) (Enzyme Res. Lab., Cat# HP1002) working solution: Diluted FII to 4.85 mg/mL in assay buffer (without BSA), stored at $-80°$ C.

Phospholipid (PCPS) vesicles:
  PCPS vesicles (80%PC, 20%PS) were prepared by modification of the method reported by Barenholz et al., *Biochemistry* (1977), Vol. 16, pp. 2806–2810.
    Phosphatidyl serine (Avanti Polar Lipids, Inc., Cat#840032):
      10 mg/mL in chloroform, purified from brain, stored $-20°$ C. under nitrogen or argon.
    Phosphatidyl Choline (Avanti Polar Lipids, Inc., Cat# 850457):
      50 mg/ml in chloroform, synthetic 16:0-18:1 Palmitoyl-Oleoyl, stored at $-20°$ C. under nitrogen or argon.

Spectrozyme-TH (American Diagnostica Inc., Cat# 238L, 50 imoles, stored at room temperature) working solution: Dissolved 50 µmoles in 10 mL $dH_2O$.
BSA (Sigma Chem Co., Cat# A-7888, FractionV, RIA grade).
Assay buffer: 50 mM TrisHCl, pH 7.5, 150 mM NaCl, 2.5 mM $CaCl_2$, 0.1% PEG 6000 (BDH), 0.05% BSA (Sigma, Fr.V, RIA grade).
For one plate assay, prepare the following working solutions:

1. Prothrombinase complex:
   (a) 100 µM PCPS (27.5 µl of PCPS stock (4.36 mM) diluted to final 1200 µl with assay buffer.
   (b) 25 nM Human factor Va: 5.08 µl of Va stock(1 mg/mL) was diluted to final 1200 µl with assay buffer.
   (c) 5 pM Human factor Xa: Dilute factor Xa stock (0.281 mg/mL) 1:1,220,000 with assay buffer. Prepare at least 1200 µl.
   Combine equal volumes (1100 µl) of each component in the order of PCPS, Va and Xa. Let stand at ambient temperature for 5 to 10 minutes and use immediately or store in ice (bring to ambient temperature before use).
2. 6 µM Human prothrombin (FII): dilute 124 µL of FII stock (4.85 mg/mL) to final 1400 µL with assay buffer.
3. 20 mM EDTA/Assay buffer: 0.8 mL of 0.5 M EDTA (pH 8.5) plus 19.2 mL assay buffer.
4. 0.2 mM Spectrozyme-TH/EDTA buffer: 0.44 mL of SPTH stock (5 mM) plus 10.56 mL of 20 mM EDTA/assay buffer.
5. Test compounds (compounds of the invention):
   Prepare a working solution (5X) from 10 mM stock (DMSO) and make a series of 1:3 dilution. Compounds were assayed at 6 concentrations in duplicate.

Assay conditions and procedure:

Prothrombinase reaction was performed in final 50 µL of mixture containing PTase (20 uM PCPS, 5 nM hFVa, and 1 pM hFXa), 1.2 uM human factor II and varied concentration of the test compounds (5 µM to 0.021 µM or lower concentration range). Reaction was started by addition of PTase and incubated for 6 minutes at room temperature. Reaction was stopped by addition of EDTA/buffer to final 10 mM. Activity of thrombin (product) was then measured in the presence of 0.1 mM of Spectrozyme-TH as substrate at 405 nm for 5 minutes (10 seconds intervals) at ambient temperature in a THEROmax microplate reader. Reactions were performed in 96-well microtiter plates.

In the first step of the assay, 10 µl of diluted test compound (5X) or buffer was added to the plates in duplicate. Then 10 µl of prothrombin (HFII) (5X) was added to each well. Next 30 µl PTase was added to each well, mix for about 30 seconds. The plates were then incubated at ambient temperature for 6 minutes.

In the next step, 50 µl of 20 mM EDTA (in assay buffer) was added to each well to stop the reaction. The resulting solutions were then mixed for about 10 seconds. Then 100 µl of 0.2 mM spectrozyme was added to each well. The thrombin reaction rate was then measured at 405 nm for 5 minutes at 10 seconds intervals in a Molecular Devices microplate reader.

Calculations:

Thrombin reaction rate was expressed as mOD/min. using OD readings from the five minute reaction. $IC_{50}$ values were calculated with the log-logit curve fit program.

The compounds of the invention demonstrated the ability to inhibit pro-thrombinase when tested in this assay.

EXAMPLE 13

(In vivo assay)

The following assay demonstrates the ability of the compounds to act as anti-coagulants.

Male rats (250–330 g) were anesthetized with sodium pentobarbital (90 mg/kg, i.p.) and prepared for surgery. The left carotid artery was cannulated for the measurement of blood pressure as well as for taking blood samples to monitor clotting variables (prothrombin time (PT) and activated partial thromboplastin time (aPTT)). The tail vein was cannulated for the purpose of administering the test compounds (i.e., the compounds of the invention and standards) and the thromboplastin infusion. The abdomen was opened via a mid-line incision and the abdominal vena cava was isolated for 2–3 cm distal to the renal vein. All venous branches in this 2–3 cm segment of the abdominal vena cava were ligated. Following all surgery, the animals were allowed to stabilize prior to beginning the experiment. Test compounds were administered as an intravenous bolus (t=0). Three minutes later (t=3), a 5-minute infusion of thromboplastin was begun. Two minutes into the infusion (t=5), the abdominal vena cava was ligated at both the proximal and distal ends. The vessel was left in place for 60 minutes, after which it was excised from the animal, slit open, the clot (if any) carefully removed, and weighed. Statistical analysis on the results was performed using a Wilcoxin-matched-pairs signed rank test.

The compounds of the invention, when tested in this assay, demonstrated the ability to clot the blood and to inhibit the clotting of the blood.

While the present invention has been described with reference to the specific embodiments thereof, it should be understood by those skilled in the art that various changes may be made and equivalents may be substituted without departing from the true spirit and scope of the invention. In addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (VII):

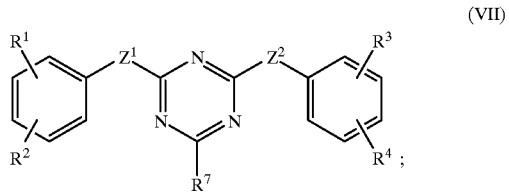

(VII)

wherein:
$Z^1$ and $Z^2$ are independently —O—, —N($R^{13}$)—, —S—, or —OCH$_2$—;

$R^1$ and $R^4$ are each independently hydrogen, halo, alkyl, nitro, —OR$^{13}$, —C(O)OR$^{13}$, —C(O)N(R$^{13}$)R$^{14}$, —N(R$^{13}$)R$^{14}$, —N(R$^{13}$)C(O)R$^{13}$, or —N(H)S(O)$_2$R$^{16}$;

$R^2$ is —C(NH)NH$_2$, —C(NH)N(H)OR$^{13}$, —C(NH)N(H)C(O)OR$^{16}$, —C(NH)N(H)C(O)R$^{13}$, —C(NH)N(H)S(O)$_2$R$^{16}$, or —C(NH)N(H)C(O)N(H)R$^{13}$;

$R^3$ is halo, alkyl, haloalkyl, nitro, amino, ureido, guanidino, —OR$^{13}$, —C(NH)NH$_2$, —C(NH)N(H)OR$^{13}$, —C(O)N(R$^{13}$)R$^{14}$, —R$^{15}$—C(O)N(R$^{13}$)R$^{14}$, —CH(OH)C(O)N(R$^{13}$)R$^{14}$, —N(R$^{13}$)R$^{14}$, —R$^{15}$—N(R$^{13}$)R$^{14}$, —C(O)OR$^{13}$, —R$^{15}$—C(O)OR$^{13}$, —N(R$^{13}$)C(O)R$^{13}$, (1,2)-tetrahydropyrimidinyl (optionally substituted by alkyl), (1,2)-imidazolyl (optionally substituted by alkyl), or (1,2)-imidazolinyl (optionally substituted by alkyl);

$R^7$ is —N(R$^9$)—(C(R$^{10}$)(R$^{11}$))$_n$—R$^{12}$ (where n is 1 to 4) or —O—(C(R$^{10}$)(R$^{11}$))$_n$—R$^{12}$ (where n is 1 to 6);

$R^9$ is hydrogen, alkyl, aryl, aralkyl, —R$^{15}$—C(O)OR$^{13}$, —R$^{15}$—C(O)N(R$^{13}$)R$^{14}$, —R$_{15}$—N(R$^{13}$)R$^{14}$, —R$^{15}$—CH(N(R$^{13}$)R$^{14}$)C(O)OR$^{13}$, or —R$^{15}$—S—(O)$_2$R$^{16}$;

each $R^{10}$ is independently alkyl, alkenyl, alkynyl, haloalkyl, haloalkenyl, cycloalkyl, cycloalkylalkyl, —C(O)OR$^{13}$, —R$^{15}$—C(O)OR$^{13}$, —R$^{15}$—C(O)N(R$^{13}$)R$^{14}$, —C(O)—R$^{15}$—N(R$^{13}$)R$^{14}$, —R$^{15}$—C(O)R$^{13}$, —R$^{15}$—C(O)N(R$^{13}$)N(R$^{13}$)R$^{14}$, —R$^{15}$—C(R$^{13}$)(OR$^{13}$)—R$^{15}$—N(R$^{13}$)(R$^{14}$), —C(R$^{13}$)(OR$^{13}$)C(O)OR$^{14}$, —R$^{15}$—C(R$^{13}$)(C(O)OR$^{13}$)$_2$, —C(R$^{13}$)(N(R$^{13}$)R$^{14}$)C(O)OR$^{13}$, —R$^{15}$—C(R$^{13}$)(N(R$^{13}$)R$^{14}$)C(O)OR$^{13}$, —C(R$^{13}$)(OR$^{13}$)R$^{14}$, —R$^{15}$—N(R$^{13}$)R$^{14}$, —R$^{15}$—N(R$^{13}$)C(O)OR$^{16}$, —R$^{15}$—N(R$^{13}$)C(O)R$^{14}$, —R$^{15}$—N(R$^{13}$)C(NR$^{13}$)R$^{16}$, —R$^{15}$—N(R$^{13}$)S(O)$_2$R$^{16}$, —R$^{15}$—N(R$^{13}$)C(O)N(R$^{13}$)R$^{14}$, —R$^{15}$—N(R$^{13}$)C(NR$^{13}$)N(R$^{13}$)R$^{14}$, —R$^{15}$—N(R$^{13}$)C(NR$^{13}$)N(R$^{13}$)N(R$^{13}$)R$^{14}$, —R$^{15}$—N(R$^{13}$)—R$^{15}$—C(R$^{13}$)(N(R$^{13}$)R$^{14}$)C(O)OR$^{13}$, —R$^{15}$—N(R$^{13}$)S(O)R$^{14}$, —R$^{15}$OR$^{13}$, —R$^{15}$—ON(R$^{13}$)C(NR$^{13}$)N(R$^{13}$)R$^{14}$, —R$^{15}$—OS(O)$_2$OR$^{13}$, —R$^{15}$—P(O)(OR$^{13}$)R$^{14}$, —R$^{15}$—OP(O)(OR$^{13}$)$_2$, —R$^{15}$—P(O)(OR$^{13}$)$_2$, —R$^{15}$—SR$^{13}$, —R$^{15}$—S—R$^{15}$—C(O)OR$^{13}$, —R$^{15}$—S—R$^{15}$—N(R$^{13}$)R$^{14}$, —R$^{15}$—S—R$^{15}$—C(R$^{13}$)(N(R$^{13}$)R$^{14}$)C(O)OR$^{13}$, —R$^{15}$—S—R$^{15}$—N(R$^{13}$)C(O)OR$^{13}$, —R$^{15}$—S—R$^{15}$—N(R$^{13}$)C(O)R$^{13}$, —R$^{15}$—S—S—R$^{15}$—C(R$^{13}$)(N(R$^{13}$)R$^{14}$)C(O)OR$^{13}$, —R$^{15}$—SC(O)N(R$^{13}$)R$^{14}$, —R$^{15}$—SC(S)N(R$^{13}$)R$^{14}$, —R$^{15}$—S(O)R$^{13}$, —R$^{15}$—S(O)$_2$R$^{16}$, —R$^{15}$—S(O)OR$^{13}$, —R$^{15}$—S(O)$_2$OR$^{13}$, —R$^{15}$—S(O)$_2$N(R$^{13}$)R$^{14}$, —R$^{15}$—S(O)(NR$^{13}$)R$^{14}$, or each $R^{10}$ is aryl (optionally substituted by one or more substituents selected from the group consisting of alkyl, halo, haloalkyl, haloalkoxy, nitro, —OR$^{13}$, —SR$^{13}$, —N(R$^{13}$)R$^{14}$, —C(O)OR$^{13}$, —C(O)N(R$^{13}$)R$^{14}$, —S(O)$_2$OR$^{13}$ and —OP(O)(OR$^{13}$)$_2$), or each $R^{10}$ is aralkyl (optionally substituted by one or more substituents selected from the group consisting of alkyl, halo, haloalkyl, haloalkoxy, cyano, nitro, —OR$^{13}$, —SR$^{13}$, —N(R$^{13}$)R$^{14}$, —C(O)OR$^{13}$, —C(O)N(R$^{13}$)R$^{14}$, —S(O)$_2$OR$^{13}$ and —OP(O)(OR$^{13}$)$_2$), or each $R^{10}$ is heterocyclyl (optionally substituted by one or more substituents selected from the group consisting of alkyl, halo, haloalkyl, haloalkoxy, aralkyl, —OR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$), or each $R^{10}$ is heterocyclylalkyl (where the heterocyclyl radical is optionally substituted by one or more substituents selected from the group consisting of alkyl, halo, haloalkyl, haloalkoxy, aralkyl, —OR$^{13}$, —SR$^{13}$, —C(O)OR$^{13}$, —N(R$^{13}$)R$^{14}$, —C(O)N(R$^{13}$)R$^{14}$), —S(O)$_2$OR$^{13}$ and —OP(O)(OR$^{13}$)$_2$), or each $R^{10}$ is adamantyl (optionally substituted by alkyl, halo, haloalkyl, haloalkoxy, —OR$^{13}$, —SR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$), or each $R^{10}$ is adamantylalkyl (where the adamantyl radical is optionally substituted by alkyl, halo, haloalkyl, haloalkoxy, —OR$^{13}$, —SR$^3$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$);

each $R^{11}$ is independently hydrogen, alkyl, cycloalkyl, or aryl;

$R^{12}$ is —C(O)OR$^{13}$ or —C(O)N(R$^{13}$)R$^{14}$;

each $R^{13}$ and $R^{14}$ is independently hydrogen, alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);

$R^{15}$ is a straight or branched alkylene chain; and $R^{16}$ is alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);

as a single stereoisomer or a mixture thereof; or a pharmaceutically acceptable salt thereof.

2. A pharmaceutical composition useful in treating a human having a disease-state characterized by thrombotic activity, which composition comprises a therapeutically effective amount of a compound of formula (VII):

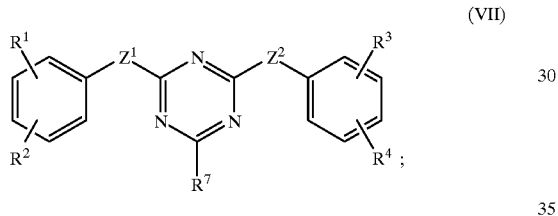

(VII)

wherein:

$Z^1$ and $Z^2$ are independently —O—, —N($R^{13}$)—, —S—, or —OCH$_2$—;

$R^1$ and $R^4$ are each independently hydrogen, halo, alkyl, nitro, —OR$^{13}$, —C(O)OR$^{13}$, —C(O)N(R$^{13}$)R$^{14}$, —N(R$^{13}$)R$^{14}$, —N(R$^{13}$)C(O)R$^{13}$, or —N(H)S(O)$_2$R$^{16}$;

$R^2$ is —C(NH)NH$_2$, —C(NH)N(H)OR$^{13}$, —C(NH)N(H)C(O)OR$^{16}$, —C(NH)N(H)C(O)R$^{13}$, —C(NH)N(H)S(O)$_2$R$^{16}$, or —C(NH)N(H)C(O)N(H)R$^{13}$;

$R^3$ is halo, alkyl, haloalkyl, nitro, amino, ureido, guanidino, —OR$^{13}$, —C(NH)NH$_2$, —C(NH)N(H)OR$^{13}$, —C(O)N(R$^{13}$)R$^{14}$, —R$^{15}$—C(O)N(R$^{13}$)R$^{14}$, —CH(OH)C(O)N(R$^{13}$)R$^{14}$, —N(R$^{13}$)R$^{14}$, —R$^{15}$—N(R$^{13}$)R$^{14}$, —C(O)OR$^{13}$, —R$^{15}$—C(O)OR$^{13}$, —N(R$^{13}$)C(O)R$^{13}$, (1,2)-tetrahydropyrimidinyl (optionally substituted by alkyl), (1,2)-imidazolyl (optionally substituted by alkyl), or (1,2)-imidazolinyl (optionally substituted by alkyl);

$R^7$ is —N(R$^9$)—(C(R$^{10}$)(R$^{11}$))$_n$—R$^{12}$ (where n is 1 to 4) or —O—(C(R$^{10}$)(R$^{11}$))$_n$—R$^{12}$ (where n is 1 to 6);

$R^9$ is hydrogen, alkyl, aryl, aralkyl, —R$^{15}$—C(O)OR$^{13}$, —R$^{15}$—C(O)N(R$^{13}$)R$^{14}$, —R$^{15}$—N(R$^{13}$)R$^{14}$, —R$^{15}$—CH(N(R$^{13}$)R$^{14}$)C(O)OR$^{13}$, or —R$^{15}$—S(O)$_2$R$^{16}$;

each $R^{10}$ is independently alkyl, alkenyl, alkynyl, haloalkyl, haloalkenyl, cycloalkyl, cycloalkylalkyl, —C(O)OR$^{13}$, —R$^{15}$—C(O)OR$^{13}$, —R$^{15}$—C(O)N(R$^{13}$)R$^{14}$, —C(O)—R$^{15}$—N(R$^{13}$)R$^{14}$, —R$^{15}$—C(O)R$^{13}$, —R$^{15}$—C(O)N(R$^{13}$)N(R$^{13}$)R$^{14}$, —R$^{15}$—C(R$^{13}$)(OR$^{13}$)—R$^{15}$—N(R$^{13}$)(R$^{14}$), —C(R$^{13}$)(OR$^{13}$)C(O)OR$^{14}$, —R$^{16}$—C(R$^{13}$)(C(O)OR$^{13}$)$_2$, —C(R$^{13}$)(N(R$^{13}$)R$^{14}$)C(O)OR$^{13}$, —R$^{15}$—C(R$^{13}$)(N(R$^{13}$)R$^{14}$)C(O)OR$^{13}$, —C(R$^{13}$)(OR$^{13}$)R$^{14}$, —R$^{15}$—N(R$^{13}$)R$^{14}$, —R$^{15}$—N(R$^{13}$)C(O)OR$^{16}$, —R$^{15}$—N(R$^{13}$)C(O)R$^{14}$, —R$^{15}$—N(R$^{13}$)C(NR$^{13}$)R$^{16}$, —R$^{15}$—N(R$^{13}$)S(O)$_2$R$^{16}$, —R$^{15}$—N(R$^{13}$)C(O)N(R$^{13}$)R$^{14}$, —R$^{15}$—N(R )C(NR )N(R$^{13}$)R$^{14}$, —R$^{15}$—N(R$^{13}$)C(NR$^{13}$)N(R$^{13}$)N(R$^{13}$)R$^{14}$, —R$^{15}$—N(R$^{13}$)—R$^{15}$—C(R$^{13}$)(N(R$^{13}$)R$^{14}$)C(O)OR$^{13}$, —R$^{15}$—N(R$^{13}$)S(O)R$^{14}$, —R$^{15}$OR$^{13}$, —R$^{16}$—ON(R$^{13}$)C(NR$^{13}$)N(R$^{13}$)R$^{14}$, —R$^{15}$—OS(O)$_2$OR$^{13}$, —R$^{15}$—P(O)(OR$^{13}$)R$^{14}$, —R$^{15}$—OP(O)(OR$^{13}$)$_2$, —R$^{15}$—P(O)(OR$^{13}$)$_2$, —R$^{15}$—SR$^{13}$, —R$^{15}$—S—R$^{15}$—C(O)OR$^{13}$, —R$^{15}$—S—R$^{15}$—N(R$^{13}$)R$^{14}$, —R$^{15}$—S—R$^{15}$—C(R$^{13}$)(N(R$^{13}$)R$^{14}$)C(O)OR$^{13}$, —R$^{15}$—S—R$^{15}$—N(R$^{13}$)C(O)OR$^{13}$, —R$^{15}$—S—R$^{15}$—N(R$^{13}$)C(O)R$^{13}$, —R$^{15}$—S—S—R$^{15}$—C(R$^3$)(N(R$^{13}$)R$^{14}$)C(O)OR$^{13}$, —R$^{15}$—SC(O)N(R$^{13}$)R$^{14}$, —R$^{16}$—SC(S)N(R$^{13}$)R$^{14}$, —R$^{15}$—S(O)R$^{13}$, —R$^{15}$—S(O)$_2$R$^{16}$, —R$^{15}$—S(O)OR$^{13}$, —R$^{15}$—S(O)$_2$OR$^{13}$, —R$^{15}$—S(O)$_2$N(R$^{13}$)R$^{14}$, —R$^{15}$—S(O)(NR$^{13}$)R$^{14}$, or each $R^{10}$ is aryl (optionally substituted by one or more substituents selected from the group consisting of alkyl, halo, haloalkyl, haloalkoxy, nitro, —OR$^{13}$, —SR$^{13}$, —N(R$^{13}$)R$^{14}$, —C(O)OR$^{13}$, —C(O)N(R$^{13}$)R$^{14}$, —S(O)$_2$OR$^{13}$ and —OP(O)(OR$^{13}$)$_2$), or each $R^{10}$ is aralkyl (optionally substituted by one or more substituents selected from the group consisting of alkyl, halo, haloalkyl, haloalkoxy, cyano, nitro, —OR$^{13}$, —SR$^{13}$, —N(R$^{13}$)R$^{14}$, —C(O)OR$^{13}$, —C(O)N(R$^{13}$)R$^{14}$, —S(O)$_2$OR$^{13}$ and —OP(O)(OR$^{13}$)$_2$), or each $R^{10}$ is heterocyclyl (optionally substituted by one or more substituents selected from the group consisting of alkyl, halo, haloalkyl, haloalkoxy, aralkyl, —OR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$), or each $R^{10}$ is heterocyclylalkyl (where the heterocyclyl radical is optionally substituted by one or more substituents selected from the group consisting of alkyl, halo, haloalkyl, haloalkoxy, aralkyl, —OR$^{13}$, —SR$^{13}$, —C(O)OR$^{13}$, —N(R$^{13}$)R$^{14}$, —C(O)N(R$^{13}$)R$^{14}$), —S(O)$_2$OR$^{13}$ and —OP(O)(OR$^{13}$)$_2$), or each $R^{10}$ is adamantyl (optionally substituted by alkyl, halo, haloalkyl, haloalkoxy, —OR$^{13}$, —SR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$), or each $R^{10}$ is adamantylalkyl (where the adamantyl radical is optionally substituted by alkyl, halo, haloalkyl, haloalkoxy, —OR$^{13}$, —SR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$);

each $R^{11}$ is independently hydrogen, alkyl, cycloalkyl, or aryl;

$R^{12}$ is —C(O)OR$^{13}$ or —C(O)N(R$^{13}$)R$^{14}$;

each $R^{13}$ and $R^{14}$ is independently hydrogen, alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);

$R^{15}$ is a straight or branched alkylene chain; and $R^{16}$ is alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);

as a single stereoisomer or a mixture thereof; or a pharmaceutically acceptable salt thereof, and a pharmaceutically acceptable excipient.

3. A method of treating a human having a disease—state characterized by thrombotic activity, which method comprises administering to a human in need thereof a therapeutically effective amount of a compound of formula (VII):

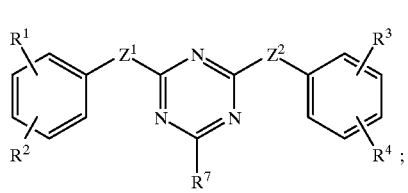

(VII)

wherein:
- $Z^1$ and $Z^2$ are independently —O—, —N($R^{13}$)—, —S—, or —OCH$_2$—;
- $R^1$ and $R^4$ are each independently hydrogen, halo, alkyl, nitro, —OR$^{13}$, —C(O)OR$^{13}$, —C(O)N(R$^{13}$)R$^{14}$, —N(R$^{13}$)R$^{14}$, —N(R$^{13}$)C(O)R$^{13}$, or —N(H)S(O)$_2$R$^{16}$;
- $R^2$ is —C(NH)NH$_2$, —C(NH)N(H)OR$^{13}$, —C(NH)N(H)C(O)OR$^{16}$, —C(NH)N(H)C(O)R$^{13}$, —C(NH)N(H)S(O)$_2$R$^{16}$, or —C(NH)N(H)C(O)N(H)R$^{13}$;
- $R^3$ is halo, alkyl, haloalkyl, nitro, amino, ureido, guanidino, —OR$^3$, —C(NH)NH$_2$, —C(NH)N(H)OR$^{13}$, —C(O)N(R$^{13}$)R$^{14}$, —R$^{15}$—C(O)N(R$^{13}$)R$^{14}$, —CH(OH)C(O)N(R$^{13}$)R$^{14}$, —N(R$^{13}$)R$^{14}$, —R$^{15}$—N(R$^{13}$)R$^{14}$, —C(O)OR$^{13}$, —R$^{15}$—C(O)OR$^{13}$, —N(R$^{13}$)C(O)R$^{13}$, (1,2)-tetrahydropyrimidinyl (optionally substituted by alkyl), (1,2)-imidazolyl (optionally substituted by alkyl), or (1,2)-imidazolinyl (optionally substituted by alkyl);
- $R^7$ is —N(R$^9$)—(C(R$^{10}$)(R$^{11}$))$_n$—R$^{12}$ (where n is 1 to 4) or —O—(C(R$^{10}$)(R$^{11}$))$_n$—R$^{12}$ (where n is 1 to 6);
- $R^9$ is hydrogen, alkyl, aryl, aralkyl, —R$^{15}$—C(O)OR$^{13}$, —R$^{15}$—C(O)N(R$^{13}$)R$^{14}$, —R$^{15}$—N(R$^{13}$)R$^{14}$, —R$^{15}$—CH(N(R$^{13}$)R$^{14}$)C(O)OR$^{13}$, or —R$^{15}$—S(O)$_2$R$^{16}$;
- each $R^{10}$ is independently alkyl, alkenyl, alkynyl, haloalkyl, haloalkenyl, cycloalkyl, cycloalkylalkyl, —C(O)OR$^{13}$, —R$^{15}$—C(O)OR$^{13}$, —R$^{15}$—C(O)N(R$^{13}$)R$^{14}$, —C(O)—R$^{15}$—N(R$^{13}$)R$^{14}$, —R$^{15}$—C(O)R$^{13}$, —R$^{15}$—C(O)N(R$^{13}$)N(R$^{13}$)R$^{14}$, —R$^{15}$—C(R$^{13}$)(OR$^{13}$)—R$^{15}$—N(R$^{13}$)(R$^{14}$), —C(R$^{13}$)(OR$^{13}$)C(O)OR$^{14}$, —R$^{15}$—C(R$^{13}$)(C(O)OR$^{13}$)$_2$, —C(R$^{13}$)(N(R$^{13}$)R$^{14}$)C(O)OR$^{13}$, —R$^{15}$—C(R$^{13}$)(N(R$^{13}$)R$^{14}$)C(O)OR$^{13}$, —C(R$^{13}$)(OR$^{13}$)R$^{14}$, —R$^{15}$—N(R$^{13}$)R$^{14}$, —R$^{15}$—N(R$^{13}$)C(O)OR$^{16}$, —R$^{15}$—N(R$^{13}$)C(O)R$^{14}$, —R$^{15}$—N(R$^{13}$)C(NR$^{13}$)R$^{16}$, —R$^{15}$—N(R$^{13}$)S(O)$_2$R$^{16}$, —R$^{15}$—N(R$^{13}$)C(O)N(R$^{13}$)R$^{14}$, —R$^{15}$—N(R$^{13}$)C(NR$^{13}$)N(R$^{13}$)R$^{14}$, —R$^{15}$—N(R$^{13}$)C(NR$^{13}$)N(R$^{13}$)N(R$^{13}$)R$^{14}$, —R$^{15}$—N(R$^{13}$)—R$^{15}$—C(R$^{13}$)(N(R$^{13}$)R$^{14}$)C(O)OR$^{13}$, —R$^{15}$—N(R$^{13}$)S(O)R$^{14}$, —R$^{15}$OR$^{13}$, —R$^{15}$—ON(R$^{13}$)C(NR$^{13}$)N(R$^{13}$)R$^{14}$, —R$^{15}$—OS(O)$_2$OR$^{13}$, —R$^{15}$—P(O)(OR$^{13}$)R$^{14}$, —R$^{15}$—OP(O)(OR$^{13}$)$_2$, —R$^{15}$—P(O)(OR$^{13}$)$_2$, —R$^{15}$—SR$^{13}$, —R$^{15}$—S—R$^{15}$—C(O)OR$^{13}$, —R$^{15}$—S—R$^{15}$—N(R$^{13}$)R$^{14}$, —R$^{15}$—S—R$^{15}$—C(R$^{13}$)(N(R$^{13}$)R$^{14}$)C(O)OR$^{13}$, —R$^{15}$—S—R$^{15}$—N(R$^{13}$)C(O)OR$^{13}$, —R$^{15}$—S—R$^{15}$—N(R$^{13}$)C(O)R$^{13}$, —R$_{15}$—S—S—R$^{15}$—C(R$^{13}$)(N(R$^{13}$)R$^{14}$)C(O)OR$^{13}$, —R$^{15}$—SC(O)N(R$^{13}$)R$^{14}$, —R$^{15}$—SC(S)N(R$^{13}$)R$^{14}$, —R$^{15}$—S(O)R$^{13}$, —R$^{15}$—S(O)$_2$R$^{16}$, —R$^{15}$—S(O)OR$^{13}$, —R$^{15}$—S(O)$_2$OR$^{13}$, —R$^{15}$—S(O)$_2$N(R$^{13}$)R$^{14}$, —R$^{15}$—S(O)(NR$^{13}$)R$^{14}$,

- or each $R^{10}$ is aryl (optionally substituted by one or more substituents selected from the group consisting of alkyl, halo, haloalkyl, haloalkoxy, nitro, —OR$^{13}$, —SR$^{13}$, —N(R$^{13}$)R$^{14}$, —C(O)OR$^{13}$, —C(O)N(R$^{13}$)R$^{14}$, —S(O)$_2$OR$^{13}$ and —OP(O)(OR$^{13}$)$_2$),
- or each $R^{10}$ is aralkyl (optionally substituted by one or more substituents selected from the group consisting of alkyl, halo, haloalkyl, haloalkoxy, cyano, nitro, —OR$^{13}$, —SR$^{13}$, —N(R$^{13}$)R$^{14}$, —C(O)OR$^{13}$, —C(O)N(R$^{13}$)R$^{14}$, —S(O)$_2$OR$^{13}$ and —OP(O)(OR$^{13}$)$_2$),
- or each $R^{10}$ is heterocyclyl (optionally substituted by one or more substituents selected from the group consisting of alkyl, halo, haloalkyl, haloalkoxy, aralkyl, —OR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$),
- or each $R^{10}$ is heterocyclylalkyl (where the heterocyclyl radical is optionally substituted by one or more substituents selected from the group consisting of alkyl, halo, haloalkyl, haloalkoxy, aralkyl, —OR$^{13}$, —SR$^{13}$, —C(O)OR$^{13}$, —N(R$^{13}$)R$^{14}$, —C(O)N(R$^{13}$)R$^{14}$), —S(O)$_2$OR$^{13}$ and —OP(O)(OR$^{13}$)$_2$),
- or each $R^{10}$ is adamantyl (optionally substituted by alkyl, halo, haloalkyl, haloalkoxy, —OR$^{13}$, —SR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$),
- or each $R^{10}$ is adamantylalkyl (where the adamantyl radical is optionally substituted by alkyl, halo, haloalkyl, haloalkoxy, —OR$^{13}$, —SR$^{13}$, —C(O)OR$^{13}$, —N(R$^{13}$)R$^{14}$, —C(O)N(R$^{13}$)R$^{14}$, —S(O)$_2$OR$^{13}$ and —OP(O)(OR$^{13}$)$_2$);
- each $R^{11}$ is independently hydrogen, alkyl, cycloalkyl, or aryl;
- $R^{12}$ is —C(O)OR$^{13}$ or —C(O)N(R$^{13}$)R$^{14}$;
- each $R^{13}$ and $R^{14}$ is independently hydrogen, alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);
- $R^{15}$ is a straight or branched alkylene chain; and
- $R^{16}$ is alkyl, aryl (optionally substituted by halo, alkyl, hydroxy, alkoxy, aralkoxy, amino, dialkylamino, monoalkylamino, nitro, cyano, carboxy, alkoxycarbonyl, aminocarbonyl, monoalkylaminocarbonyl, or dialkylaminocarbonyl), or aralkyl (optionally substituted by halo, alkyl, aryl, hydroxy, alkoxy, aralkyl, amino, dialkylamino, monoalkylamino, nitro, cyano, carboxy, alkoxycarbonyl, aminocarbonyl, monoalkylaminocarbonyl, or dialkylaminocarbonyl);

as a single stereoisomer or a mixture thereof; or a pharmaceutically acceptable salt thereof.

* * * * *